(12) United States Patent
Kostem

(10) Patent No.: US 12,106,828 B2
(45) Date of Patent: *Oct. 1, 2024

(54) SYSTEMS AND DEVICES FOR SIGNAL CORRECTIONS IN PIXEL-BASED SEQUENCING

(71) Applicant: Illumina, Inc., San Diego, CA (US)

(72) Inventor: Emrah Kostem, Menlo Park, CA (US)

(73) Assignee: Illumina, Inc., San Diego, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/703,975

(22) Filed: Mar. 24, 2022

(65) Prior Publication Data
US 2022/0245455 A1 Aug. 4, 2022

Related U.S. Application Data

(63) Continuation of application No. 16/874,599, filed on May 14, 2020, now Pat. No. 11,423,306.
(Continued)

(51) Int. Cl.
*G06V 10/50* (2022.01)
*G06N 3/04* (2023.01)
(Continued)

(52) U.S. Cl.
CPC ............... *G16B 40/10* (2019.02); *G06N 3/04* (2013.01); *G06N 3/048* (2023.01); *G06N 3/08* (2013.01); *G06V 10/507* (2022.01)

(58) Field of Classification Search
CPC ............ C12Q 1/6869; G01N 21/6428; G01N 21/6454; G06V 10/507; G16B 30/00; G16B 40/10
See application file for complete search history.

(56) References Cited

U.S. PATENT DOCUMENTS 5,641,658 A   6/1997   Adams et al.
6,090,592 A   7/2000   Adams et al.
(Continued)

FOREIGN PATENT DOCUMENTS

CA   2894317 A1   12/2016
CA   3104851 A1   11/2020
(Continued)

OTHER PUBLICATIONS

Wang et al., An adaptive decorrelation method removes Illumina DNA base-calling errors caused by crosstalk between adjacent clusters, Scientific Reports, published Feb. 20, 2017, 11 pages.
(Continued)

*Primary Examiner* — Ian L Lemieux
(74) *Attorney, Agent, or Firm* — Keller Preece PLLC

(57) ABSTRACT

The technology disclosed relates to determining tag signals from measured intensities for purposes of base calling in next-generation sequencing. In particular, the measured intensities are collected by light sensors in a sensor array directed to a sample surface including pixel areas and holding a plurality of clusters during a sequence of sampling events. Each light sensor is directed to and measuring intensity from one of the pixel areas during each sampling event. The method includes adjusting the measured intensities from a pixel in the pixel areas for background intensity based on variations in background levels of the light sensors in the sensor array and determining an intensity of a tag signal originating from the pixel based on the adjusted measured intensities of the pixel.

20 Claims, 21 Drawing Sheets
(11 of 21 Drawing Sheet(s) Filed in Color)

Related U.S. Application Data

(60) Provisional application No. 62/849,091, filed on May 16, 2019, provisional application No. 62/849,132, filed on May 16, 2019, provisional application No. 62/849,133, filed on May 16, 2019.

(51) Int. Cl.
*G06N 3/048* (2023.01)
*G06N 3/08* (2023.01)
*G16B 40/10* (2019.01)

(56) References Cited

U.S. PATENT DOCUMENTS

| | | |
|---|---|---|
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,576,371 B1 | 8/2009 | Goushcha |
| 7,592,435 B2 | 9/2009 | Milton et al. |
| 8,182,993 B2 | 5/2012 | Tomaney et al. |
| 8,241,573 B2 | 8/2012 | Banerjee et al. |
| 8,392,126 B2 | 3/2013 | Mann |
| 8,401,258 B2 | 3/2013 | Hargrove et al. |
| 8,407,012 B2 | 3/2013 | Erlich et al. |
| 8,594,439 B2 | 11/2013 | Staelin et al. |
| 8,725,425 B2 | 5/2014 | Heiner et al. |
| 8,795,971 B2 | 8/2014 | Kersey et al. |
| 8,965,076 B2 | 2/2015 | Garcia et al. |
| 9,279,154 B2 | 3/2016 | Previte et al. |
| 9,453,258 B2 | 9/2016 | Kain et al. |
| 9,708,656 B2 | 7/2017 | Turner et al. |
| 9,770,713 B2 * | 9/2017 | Haga .............. C12Q 1/6869 |
| 10,023,911 B2 | 7/2018 | Tomaney et al. |
| 10,068,054 B2 | 9/2018 | Van Rooyen et al. |
| 10,152,776 B2 | 12/2018 | Langlois et al. |
| 10,168,438 B2 | 1/2019 | Dennis et al. |
| 10,241,075 B2 | 3/2019 | Davey et al. |
| 10,354,747 B1 | 7/2019 | DePristo et al. |
| 10,423,861 B2 | 9/2019 | Gao et al. |
| 10,491,239 B1 | 11/2019 | Hubara |
| 10,527,549 B2 | 1/2020 | Rebetez et al. |
| 10,540,591 B2 | 1/2020 | Gao et al. |
| 10,619,195 B2 | 4/2020 | Lamb et al. |
| 10,648,027 B2 | 5/2020 | Mannion et al. |
| 10,711,299 B2 | 7/2020 | Rothberg et al. |
| 10,713,794 B1 | 7/2020 | He et al. |
| 10,740,880 B2 | 8/2020 | Paik et al. |
| 10,740,883 B2 | 8/2020 | Zerfass et al. |
| 10,755,810 B2 | 8/2020 | Buckler et al. |
| 10,963,673 B2 | 3/2021 | Schaumberg et al. |
| 11,138,496 B2 | 10/2021 | Seth |
| 11,593,649 B2 | 2/2023 | Kostem |
| 11,817,182 B2 | 11/2023 | Kostem |
| 2002/0055100 A1 | 5/2002 | Kawashima et al. |
| 2003/0062485 A1 | 4/2003 | Fernandez et al. |
| 2004/0002090 A1 | 1/2004 | Mayer et al. |
| 2004/0096853 A1 | 5/2004 | Mayer |
| 2006/0014151 A1 | 1/2006 | Ogura et al. |
| 2006/0040297 A1 | 2/2006 | Leamon et al. |
| 2006/0064248 A1 | 3/2006 | Saidi et al. |
| 2006/0188901 A1 | 8/2006 | Barnes et al. |
| 2006/0210984 A1 * | 9/2006 | Lambert ............ C12Q 1/6813 435/7.1 |
| 2006/0240439 A1 | 10/2006 | Smith et al. |
| 2006/0269130 A1 | 11/2006 | Maroy et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0234136 A1 | 9/2008 | Ormanac et al. |
| 2008/0242560 A1 | 10/2008 | Gunderson et al. |
| 2009/0081775 A1 | 3/2009 | Hodneland et al. |
| 2010/0046830 A1 | 2/2010 | Wang et al. |
| 2010/0111370 A1 | 5/2010 | Black et al. |
| 2010/0157086 A1 | 6/2010 | Segale et al. |
| 2011/0059865 A1 | 3/2011 | Smith et al. |
| 2011/0065607 A1 | 3/2011 | Kersey et al. |
| 2011/0281736 A1 | 11/2011 | Ormanac et al. |
| 2011/0286628 A1 | 11/2011 | Goncalves et al. |
| 2011/0295902 A1 | 12/2011 | Mande et al. |
| 2012/0015825 A1 | 1/2012 | Zhong et al. |
| 2012/0020537 A1 | 1/2012 | Garcia et al. |
| 2012/0109598 A1 * | 5/2012 | Davey ................ C12Q 1/6874 703/2 |
| 2013/0015370 A1 * | 1/2013 | Damaskinos ....... G01N 21/6452 250/200 |
| 2013/0059740 A1 | 3/2013 | Ormanac et al. |
| 2013/0079232 A1 | 3/2013 | Kain et al. |
| 2013/0124100 A1 | 5/2013 | Drmanac et al. |
| 2013/0188866 A1 | 7/2013 | Obrador et al. |
| 2013/0250407 A1 | 9/2013 | Schaffer et al. |
| 2014/0051588 A9 | 2/2014 | Ormanac et al. |
| 2014/0152801 A1 | 6/2014 | Fine et al. |
| 2014/0303016 A1 * | 10/2014 | Tomaney ............ G01N 21/6428 702/20 |
| 2014/0329699 A1 * | 11/2014 | Esfandyarpour .... C12Q 1/6844 204/600 |
| 2015/0079596 A1 | 3/2015 | Eltoukhy et al. |
| 2015/0117784 A1 | 4/2015 | Lin et al. |
| 2015/0169824 A1 | 6/2015 | Kermani et al. |
| 2015/0177148 A1 * | 6/2015 | Estrada .............. G01N 21/6486 250/459.1 |
| 2016/0042511 A1 | 2/2016 | Chukka et al. |
| 2016/0078272 A1 | 3/2016 | Hammoud |
| 2016/0110498 A1 | 4/2016 | Bruand et al. |
| 2016/0133668 A1 * | 5/2016 | Rothberg .......... H01L 27/14603 250/206 |
| 2016/0196479 A1 | 7/2016 | Chertok et al. |
| 2016/0350914 A1 | 12/2016 | Champlin et al. |
| 2016/0356715 A1 | 12/2016 | Zhong et al. |
| 2016/0357903 A1 | 12/2016 | Shendure et al. |
| 2016/0371431 A1 | 12/2016 | Haque et al. |
| 2017/0044601 A1 | 2/2017 | Crnogorac et al. |
| 2017/0098032 A1 | 4/2017 | Desai et al. |
| 2017/0116520 A1 | 4/2017 | Min et al. |
| 2017/0161545 A1 | 6/2017 | Champlin et al. |
| 2017/0169313 A1 | 6/2017 | Choi et al. |
| 2017/0175174 A1 * | 6/2017 | Chiu ..................... G01N 21/47 |
| 2017/0249421 A1 | 8/2017 | Eberle et al. |
| 2017/0249744 A1 | 8/2017 | Wang et al. |
| 2017/0362634 A1 | 12/2017 | Ota et al. |
| 2018/0075279 A1 | 3/2018 | Gertych et al. |
| 2018/0107927 A1 | 4/2018 | Frey |
| 2018/0114337 A1 | 4/2018 | Li et al. |
| 2018/0189613 A1 | 7/2018 | Wolf et al. |
| 2018/0195953 A1 | 7/2018 | Langlois et al. |
| 2018/0201992 A1 | 7/2018 | Wu et al. |
| 2018/0211001 A1 | 7/2018 | Gopalan et al. |
| 2018/0274023 A1 | 9/2018 | Belitz et al. |
| 2018/0274028 A1 * | 9/2018 | Staker .................... G06V 20/69 |
| 2018/0305751 A1 | 10/2018 | Vermaas et al. |
| 2018/0322327 A1 | 11/2018 | Smith et al. |
| 2018/0330824 A1 | 11/2018 | Athey |
| 2018/0334711 A1 | 11/2018 | Kelley et al. |
| 2018/0334712 A1 | 11/2018 | Singer et al. |
| 2018/0340234 A1 | 11/2018 | Scafe et al. |
| 2019/0034586 A1 | 1/2019 | Pirrotte et al. |
| 2019/0080450 A1 | 3/2019 | Arar et al. |
| 2019/0107642 A1 | 4/2019 | Farhadi Nia et al. |
| 2019/0114544 A1 | 4/2019 | Sundaram et al. |
| 2019/0156915 A1 | 5/2019 | Zhang et al. |
| 2019/0164010 A1 | 5/2019 | Ma et al. |
| 2019/0170680 A1 | 6/2019 | Sikora et al. |
| 2019/0180153 A1 | 6/2019 | Buckler et al. |
| 2019/0213473 A1 | 7/2019 | Dutta et al. |
| 2019/0237160 A1 | 8/2019 | Rothberg et al. |
| 2019/0237163 A1 | 8/2019 | Wang et al. |
| 2019/0244348 A1 | 8/2019 | Buckler et al. |
| 2019/0266491 A1 | 8/2019 | Gao et al. |

(56) References Cited

U.S. PATENT DOCUMENTS

| | | |
|---|---|---|
| 2019/0272638 A1 | 9/2019 | Mouton et al. |
| 2019/0332118 A1 | 10/2019 | Wang et al. |
| 2019/0392578 A1 | 12/2019 | Chukka et al. |
| 2020/0027002 A1 | 1/2020 | Hickson et al. |
| 2020/0054306 A1 | 2/2020 | Mehanian et al. |
| 2020/0057838 A1 | 2/2020 | Yekhanin et al. |
| 2020/0065675 A1 | 2/2020 | Sundaram et al. |
| 2020/0125947 A1 | 4/2020 | Park et al. |
| 2020/0176082 A1 | 6/2020 | Massingham |
| 2020/0193597 A1 | 6/2020 | Fan et al. |
| 2020/0226368 A1 | 7/2020 | Bakalo et al. |
| 2020/0256856 A1 | 8/2020 | Chou et al. |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0320294 A1 | 10/2020 | Mangal et al. |
| 2020/0342955 A1 | 10/2020 | Guo et al. |
| 2020/0364565 A1 | 11/2020 | Kostem |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0334957 A1* | 10/2021 | Ballinger .............. G06T 7/0012 |
| 2021/0390278 A1 | 12/2021 | Van Leeuwen et al. |

FOREIGN PATENT DOCUMENTS

| | | | |
|---|---|---|---|
| CN | 102985803 | A | 3/2013 |
| CN | 105473998 | A | 4/2016 |
| CN | 105980578 | A | 9/2016 |
| CN | 109614981 | A | 4/2019 |
| CN | 110245685 | A | 11/2020 |
| EP | 3130681 | A1 | 2/2017 |
| EP | 3373238 | A1 | 9/2018 |
| JP | 2007199397 | A | 8/2007 |
| WO | 9106678 | A1 | 5/1991 |
| WO | 2005065814 | A1 | 7/2005 |
| WO | 2006064199 | A1 | 6/2006 |
| WO | 2007123744 | A2 | 11/2007 |
| WO | 2008154317 | A1 | 12/2008 |
| WO | 2012058096 | A1 | 5/2012 |
| WO | 2014142921 | A1 | 9/2014 |
| WO | 2015084985 | A2 | 6/2015 |
| WO | 2016145516 | A1 | 9/2016 |
| WO | 2016201564 | A1 | 12/2016 |
| WO | 2017184997 | A1 | 10/2017 |
| WO | 2018129314 | A1 | 7/2018 |
| WO | 2018165099 | A1 | 9/2018 |
| WO | 2018203084 | A1 | 11/2018 |
| WO | 2019027767 | A1 | 2/2019 |
| WO | 2019028047 | A1 | 2/2019 |
| WO | 2019055856 | A1 | 3/2019 |
| WO | 2019079182 | A1 | 4/2019 |
| WO | 2019079202 | A1 | 4/2019 |
| WO | 2019090251 | A2 | 5/2019 |
| WO | 2019136284 | A1 | 7/2019 |
| WO | 2019136388 | A1 | 7/2019 |
| WO | 2019140402 | A1 | 7/2019 |
| WO | 2019147904 | A1 | 8/2019 |
| WO | 2020014280 | A1 | 1/2020 |
| WO | 2020123552 | A1 | 6/2020 |

OTHER PUBLICATIONS

Cacho et al., A comparison of Base Calling Algorithms for Illumina Sequencing Technology, dated Oct. 5, 2015, Briefings in Bioinformatics 2016 (17), 786-795.
U.S. Appl. No. 16/825,987, filed Mar. 20, 2020, U.S. Pat. No. 11,347,965, May 31, 2022, Issued.
U.S. Appl. No. 16/825,991, filed Mar. 20, 2020, U.S. Pat. No. 11,210,554, Dec. 28, 2021, Issued.
U.S. Appl. No. 16/826,126, filed Mar. 20, 2020, US-2020-0302297-A1, Sep. 24, 2020, Pending.
U.S. Appl. No. 16/826,134, filed Mar. 20, 2020, US-2020-0327377-A1, Oct. 15, 2020, Pending.
U.S. Appl. No. 16/826,168, filed Mar. 21, 2020, US-2020-0302224-A1, Sep. 24, 2020, Allowed.
U.S. Appl. No. 17/529,222, filed Nov. 17, 2021, US-2022-0147760-A1, May 12, 2022, Pending.
U.S. Appl. No. 17/827,612, filed May 27, 2022, Pending.
U.S. Appl. No. 16/874,633, filed May 14, 2020, US-2020-0364565-A1, Nov. 19, 2020, Allowed.
U.S. Appl. No. 17/175,546, filed Feb. 12, 2021, US-2021-0265009-A1, Aug. 26, 2021, Pending.
U.S. Appl. No. 17/180,542, filed Feb. 19, 2021, US-2021-0265017-A1, Aug. 26, 2021, Pending.
U.S. Appl. No. 17/176,151, filed Feb. 15, 2021, US-2021-0265018-A1, Aug. 26, 2021, Pending.
U.S. Appl. No. 17/411,980, filed Aug. 25, 2021, US-2022-0067489-A1, Mar. 3, 2022, Pending.
U.S. Appl. No. 17/687,551, filed Mar. 4, 2022, Pending.
U.S. Appl. No. 17/687,583, filed Mar. 4, 2022, Pending.
U.S. Appl. No. 17/176,147, filed Feb. 15, 2021, US-2021-0265015-A1, Aug. 26, 2021, Pending.
U.S. Appl. No. 17/179,395, filed Feb. 18, 2021, US-2021-0265016-A1, Aug. 26, 2021, Pending.
U.S. Appl. No. 17/180,480, filed Feb. 19, 2021, US-2021-0264266-A1, Aug. 26, 2021, Pending.
U.S. Appl. No. 17/180,513, filed Feb. 19, 2021, US-2021-0264267-A1, Aug. 26, 2021, Pending.
U.S. Appl. No. 17/687,586, filed Mar. 4, 2022, Pending.
U.S. Appl. No. 17/232,056, filed Apr. 15, 2021, Pending.
U.S. Appl. No. 17/468,411, filed Sep. 7, 2021, Pending.
U.S. Appl. No. 17/830,287, filed Jun. 1, 2022, Pending.
U.S. Appl. No. 17/830,316, filed Jun. 1, 2022, Pending.
U.S. Appl. No. 17/839,331, filed Jun. 13, 2022, Pending.
U.S. Appl. No. 17/703,935, filed Mar. 24, 2022, Pending.
U.S. Appl. No. 17/703,958, filed Mar. 24, 2022, Pending.
PCT/US2020/033280, May 15, 2020, WO 2020/232409, Nov. 19, 2020, Nationalized.
PCT/US2020/033281, May 15, 2020, WO 2020/232410, Nov. 19, 2020, Nationalized.
PCT/US2020/024090, Mar. 21, 2020, WO 2020/191389, Sep. 24, 2020, Nationalized.
PCT/US2020/024087, Mar. 21, 2020, WO 2020/205296, Oct. 8, 2020, Nationalized.
PCT/US2020/024088, Mar. 21, 2020, WO 2020/191387, Sep. 24, 2020, Nationalized.
PCT/US2020/024091, Mar. 21, 2020, WO 2020/191390, Sep. 24, 2020, Nationalized.
PCT/US2020/024092, Mar. 22, 2020, WO 2020/191391, Sep. 24, 2020, Nationalized.
PCT/US2021/018258, Feb. 16, 2021, Pending.
PCT/US2021/018910, Feb. 19, 2021, Pending.
PCT/US2021/018422, Feb. 17, 2021, Pending.
PCT/US2021/047763, Aug. 26, 2021, Pending.
PCT/US2022/020460, Mar. 15, 2022, Pending.
PCT/US2022/020462, Mar. 15, 2022, Pending.
PCT/US2021/018427, Feb. 17, 2021, Pending.
PCT/US2021/018913, Feb. 19, 2021, Pending.
PCT/US2021/018915, Feb. 19, 2021, Pending.
PCT/US2021/018917, Feb. 19, 2021, Pending.
PCT/US2022/021814, Mar. 24, 2022, Pending.
PCT/US2022/24911, Apr. 14, 2022, Pending.
PCT/US2022/24913, Apr. 14, 2022, Pending.
PCT/US2022/035564, Jun. 29, 2022, Pending.
PCT/US2022/035567, Jun. 29, 2022, Pending.
PCT/US2022/035847, Jun. 30, 2022, Pending.
PCT/US2022/24916, Apr. 14, 2022, Pending.
PCT/US2022/24918, Apr. 14, 2022, Pending.
Kao et al., BayesCall: A model-based base-calling algorithm for high-throughput short-read sequencing, Genome Research (19), pp. 1884-1895, dated 2009.

(56) References Cited

OTHER PUBLICATIONS

Rang et. al., From squiggle to basepair: computational approaches for improving nanopore sequencing read accuracy, Genome Biology 2018, (19), 30.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
MiSEQ: Imaging and Base Calling: Illumina, Inc. Online Training Course, colored version, [retrieved on Oct. 11, 2020], Retrieved from <URL: https://support.illumina.com/training.html >, 9 pages.
Kircher et. al., Improved base-calling for the Illumina Genome Analyzer using Machine Learning Strategies, Genome Biology, published Aug. 14, 2009, 9 pages.
Angermueller, Christof, et al., Deep learning for computational biology, Molecular Systems Biology, dated Jun. 6, 2016, 16 pages.
Smith et. al., Barcoding and demultiplexing Oxford nanopore native RNA sequencing reads with deep residual learning, bioRxiv, dated Dec. 5, 2019, 18 pages.
Aggarwal, Neural Networks and Deep Learning: A Textbook, Springer, dated Aug. 26, 2018, 512 pages.
Wang et. al., Deep Neural Network Approximation for Custom Hardware: Where We've Been, Where We're Going, Cornell University, dated Jan. 21, 2019, 37 pages.
Lavin et al., Fast Algorithms for Convolutional Neural Networks, dated Nov. 10, 2015, 9 pages.
Liu et al., A Uniform Architecture Design for Accelerating 2D and 3D CNNs on FPGAs, published Jan. 7, 2019, 19 pages.
Zeng et al., Causalcall: Nanopore Basecalling Using a Temporal Convolutional Network, dated Jan. 20, 2020, 11 pages.
Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et. al., Efficient Processing of Deep Neural Networks: A Tutorial and Survey, Cornell University Library, dated Mar. 27, 2017, 21 pages.
Jaganathan, K. et al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in pseudogenes and its evolutionary implications. J. Molec. Evol. 21, 58-71 (1984).
Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonic de novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the world's primates—why primates matter. Sc. Adv. 3, e1600946 (2017), 17 pages.
Kent, W. J. et al. The human genome browser at UCSC. Genome Res. 12, 996-1006 (2002).
Tyner, C. et al. The UCSC Genome Browser database—2017 update. Nucleic Acids Res. 45, D626-D634 (2017).
Kabsch, W., & Sander, C. Dictionary of protein secondary structure—pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6,15 (Springer, Cham, Switzerland; 2016).
Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data. Sci. Rep. 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Bentley et. al., Accurate Whole Human Genome Sequencing using Reversible Terminator Chemistry, Nature, Nov. 2008, 21 pages.
Illumina CMOS Chip and One-Channel SBS Chemistry, Illumina Inc, 2018, 4 pages.
Illumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Python Implementation of the color map function for the Pascal VOC data set, Github, 4 pages, retrieved on Jul. 23, 2021. Retrieved from [URL: https://gist.github.com/wllhf/a4533e0adebe57e3ed06d4b50c8419ae ].

(56) References Cited

OTHER PUBLICATIONS

Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et al., SegNet: A Deep Convolutional Encoder-Decoder Architecture for Image Segmentation, dated Oct. 10, 2016, 14 pages.
Li et al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et. al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et. al., Chiron: translating nanopore raw signal directly into nucleotide sequence using deep learning, dated Aug. 23, 2017, 10 pages.
Stoiber et. al., BasecRAWller: Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Ye et. al., BlindCall: ultra-fast base-calling of high-throughput sequencing data by blind deconvolution, Bioinformatics, vol. 30, No. 9, 2014, pp. 1214-1219, 6 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.
Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.
Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et. al., DeepDNA: a hybrid convolutional and recurrent neural network for compressing human mitochondrial genomes, IEEE International Conference on Bioinformatics and Biomedicine, 2018, 5 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
Eraslan et. al., "Deep Learning: New computational modelling techniques for genomics", dated Jul. 2019, 15 pages.
Assfalg et. al., "3DString, A Feature String Kernel for 3D Object Classification on Voxelized Data", dated Nov. 6, 2006. 10 pages.
Pei et al., A Topological Measurement for Weighted Protein Interaction Network, IEEE Computational Systems Bioinformatics Conference dated 2005, 11 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
Carter et al., "Cancer-specific high-throughput annotation of somatic mutations—computational prediction of driver missense mutations," Cancer research 69, No. 16 (2009) pp. 6660-6667.
Min, et al., "Deep Learning in Bioinformatics", Jun. 19, 2016, 46pgs.
Jiminez et. al., DeepSite—protein binding site predictor using 3D CNNs, dated Oct. 1, 2017, 7 pages.
Pu et. al., "DeepDrug3D: Classification of ligand-binding pockets in proteins with a convolutional neural network", dated Feb. 4, 2019, 23 pages.

(56) References Cited

OTHER PUBLICATIONS

Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et. al., "Predicting changes in protein thermostability upon mutation with deep 3D convolutional neural networks", dated Feb. 28, 2020, 21 pages.
Raschka et. al., "Machine Learning and AI-based approaches for bioactive ligand discovery and GPCR-ligand recognition", dated Jun. 6, 2020, 33 pages.
Morrone et. al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated 26 Novemeber 2017, 63 pages.
Jordan, An overview of semantic image segmentation, dated May 21, 2018, 28 pages retrieved on Jul. 21, 2021. Retrieved from the internet [URL: https://www.jeremyjordan.me/semantic-segmentation/ ].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/ ].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing-Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Illumina, An Introduction to Next-Generation Sequencing Technology, 2017, 16 pages.
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.
Rodriguez-Ezpeleta, Bioinformatics for High Throughput Sequencing, Springer, 2012, 266 pages.
Ilumina, Optimizing Cluster Density on Illumina Sequencing Systems, 2016, 12 pages.
Boza et. al., DeepNano: Deep recurrent neural networks for base calling in MinION nanopore reads, PLOS ONE, dated Jun. 5, 2017, 13 pages.
Kircher, Understanding and Improving high-throughput sequencing data production and analysis, Leipzig University, 2011, 216 pages.
Lutteropp, Error-Profile-Aware Correction of Next Generation Sequencing Reads, Karlsruhe Institute of Technology, dated Mar. 31, 2017, 96 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2, 104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Stenson, P. D. et al. The Human Gene Mutation Database—building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.

(56) References Cited

OTHER PUBLICATIONS

Ching, et. al., "Opportunities and Obstacles for Deep Learning in Biology and Medicine", May 26, 2017, 47pgs.
Gu et. al., Recent Advances in Convolutional Neural Networks, dated Jan. 5, 2017, 37 pages.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).

Schrago, C. G., & Russo, C. A. Timing the origin of New World monkeys. Mol. Biol. Evol. 20, 1620-1625 (2003).
Andrum, M. J. et al. ClinVar—public archive of interpretations of clinically relevant variants. Nucleic Acids Res. 44, D862-868 (2016).
Brandon, E. P., Idzerda, R. L. & McKnight, G. S. Targeting the mouse genome—a compendium of knockouts (Part II). Curr. Biol. 5, 758-765 (1995).
Lieschke, J. G. & Currie, P. D. Animal models of human disease—zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord et al., WAVENET: A Generative Model for Raw Audio, dated Sep. 19, 2016, 15 pages.
Arik et al., Deep Voice: Real-time Neural Text-to-Speech, dated 2017, 17 pages.
Yu et al., Multi-Scale Context Aggregation by Dilated Convolutions, ICLR 2016, dated Apr. 30, 2016, 13 pages.
He et. al., Deep Residual Learning for Image Recognition, 2015.
Srivastava et al., Highway Networks, dated 2015, 6 pages.
Huang et al., Densely Connected Convolutional Networks, dated Aug. 17, 2017, 9 pages.
Szegedy et. al., Going Deeper with Convolutions, dated 2014, 12 pages.

(56) References Cited

OTHER PUBLICATIONS

Ioffe et al., Batch Normalization Accelerating Deep Network Training by Reducing Internal Covariate Shift, dated 2015, 11 pages.
Wolterink et al., Dilated Convolutional Neural Networks for Cardiovascular MR Segmentation in Congenital Heart Disease, dated 2017, 9 pages.
Piqueras, Autoregressive Model Based on a Deep Convolutional Neural Network for Audio Generation, Tampere University of Technology, dated 2016, 58 pages.
Wu, Introduction to Convolutional Neural Networks, Nanjing University, dated 2017, 31 pages.
scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et. al., Image Segmentation with Watershed Algorithm, Revision 43532856, 2013, 6 pages. [retrieved on Jun. 8, 2021] Retrieved from the Internet <URL: https://opencv-python-tutroals.readthedocs.io/en/latest/py_tutorials/py_imgproc/py_watershed/py_watershed.html>.
Mzur, Watershed.py, Github, 3 pages. [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et al., Microscopy cell counting and detection with fully convolutional regression networks, Computer methods in biomechanics and biomedical engineering, Imaging and Visualization, 6(3), pp. 283-292, 2018.
Xie, Y., et al., Beyond classification: structured regression for robust cell detection using convolutional neural network. International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b>, 2 pages.
Assem, Predicting periodic and chaotic signals using Wavenets, Master of Science thesis, Delft University of Technology, Aug. 18, 2017, pp. 3-38.
Goodfellow et al., Chapter 9—Convolutional Networks, Deep Learning, MIT Press, dated 2016, 41 pages.
Illumina, "Indexed Sequencing Overview Guide", Document No. 15057455, v. 5, Mar. 2019.
Albrecht et. al., Deep learning for single-molecule science, Nanotechnology (28), dated 2017, 423001, 11 pages.
MiSEQ: Imaging and Base Calling: Illumina, Inc. Online Training Course, dated Jan. 1, 2013 [retrieved on Jul. 13, 2020], Retrieved from <URL: https://support.illumina.com/training.html >, 13 pages.
MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/MiSeq%20Imaging%20and%20Base%20Calling%20Script.pdf >.
Zhao et. al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
Misiunas et. al., QuipuNet: convolutional neural network for single-molecule nanopore sensing, dated May 30, 2018, 7 pages.
Boza et. al., Deep Recurrent Neural Networks for Base Calling in MinION Nanopore Reads, dated Mar. 30, 2016, 12 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res. 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expanding to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et al., "DANN—a deep learning approach for annotating the pathogenicity of genetic variants", Oct. 22, 2014, 3 pages.
Sundaram, et al., "Predicting the clinical impact of human mutation with deep neural networks", Aug. 2018, 15pgs.
Xiong, et al., "The human splicing code reveals new insights into the genetic determinants of disease", Jan. 9, 2015, 20pgs.
Yue, et al., "Deep Learning for Genomics—A Concise Overview from internet", May 8, 2018, 40pgs.

(56) References Cited

OTHER PUBLICATIONS

Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et al., "Selene—a PyTorch based deep learning library for sequence level data", Oct. 10, 2018, 15pages.
Grob, C., et al., "Predicting variant deleteriousness in non human species Applying the CADD approach in mouse", 2018, 11 pages.
Li, et al., "FoldingZero—Protein Folding from Scratch in Hydrophobic Polar Model", Dec. 3, 2018, 10 pages.
Rentzsch, et. al.,_"CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
Wei etal_The Role of Balanced Training and Testing Data Sets for Binary Classifiers in Bioinformatics dated Jul. 9, 2013 12 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.
Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
dbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation. "International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9 (2011) e24210.
Korhonen, Janne H., et al. "Fast motif matching revisited—high-order PWMs, SNPs and indels." Bioinformatics 33.4 (2016) 514-521.
Wong, Sebastien C., et al. "Understanding data augmentation for classification—when to warp?." 2016 international conference on digital image computing—techniques and applications (DICTA). IEEE, 2016.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al., ImageNet Classification with Deep Convolutional Neural Networks, 2012, 9 Pages.
Geeks for Geeks, "Underfitting and Overfilling in Machine Learning", [retrieved on Aug. 26, 2019]. Retrieved from the Internet <www.geeksforgeeks.org/underfitting-and-overfitting-in-machine-learning/>, 2 pages.
Illumina, GA Bootcamp, Sequencing Module 3: Overview, Broad Institute, 73 pages, [retrieved on Jul. 22, 2021], Retrieved from [URL: https://www.broadinstitute.org/files/shared/illuminavids/sequencingSlides.pdf].
Semantic Segmentation Examples—MATLAB and Simulink, 22 pages, [retrieved on Jul. 21, 2021], Retrieved from the Internet [URL: https://www.mathworks.com/help/vision/ug/semantic-segmentation-examples.html ].
Bentley et. al., Accurate Whole Human Genome Sequencing using Reversible Terminator Chemistry, Supplemental Information, Nature, dated Nov. 6, 2008, 55 pages, [retrieved on Jul. 21, 2021], retrieved from the internet [URL: https://media.nature.com/original/nature-assets/nature/journal/v456/n7218/extref/nature07517-s1.pdf ].
Grange, NGS: the basics, Institut Jacques Monod, dated Jun. 26, 2000, 59 pages.
Massingham et. al., All Your Base: a fast and accurate probabilistic approach to base calling, European Bioinformatics Institute, 22 pages, [retrieved on Jul. 22, 2021], Retrieved from the internet [URL: https://www.ebi.ac.uk/goldman-srv/AYB/references/ayb.pdf].
Krishnakumar et. al., Systematic and stochastic influences on the performance of the MinION nanopore sequencer across a range of nucleotide bias, Scientific Reports, published Feb. 16, 2018, 13 pages.
Tegfalk, Application of Machine Learning techniques to perform base-calling in next-generation DNA sequencing, KTH Royal Institue of Technology, dated 2020, 53 pages.
Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.
Kircher et al., Improved base-calling for the Illumina Genome Analyzer using Machine Learning Strategies, Genome Biology 2009, I O:R83, Aug. 14, 2009, 10 pages.
Albrecht etal, "Deep Learning for single-molecule science", Nanotechnology 28, IOP Publishuigm Sep. 18, 2017 11 pages.
Adriana Romero et al., FitNets: Hints for Thin Deep Nets, published Mar. 27, 2015, 13 pages.
Robinson et al., Computational Exome and Genome Analysis—Chapter 3 Illumina Technology, dated 2018, 25 pages.
Wang et al., An adaptive decorrelation method removes Illumina DNA base-calling errors caused by crosstalk between adjacent clusters—with Supplemental Materials, Scientific Reports, published Feb. 20, 2017, 17 pages.
Pfeiffer et al., Systematic evaluation of error rates and causes in short samples in next-generation sequencing, Scientific Reports, published Jul. 19, 2018, 14 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and

(56) References Cited

OTHER PUBLICATIONS machine learning methods, Computational and Structural Biotechnology Journal 18, dated Feb. 20, 2022, pp. 439-454, 16 pages.

Qbal et al., Comprehensive characterization of amino acid positions in protein structures reveals molecular effects of missense variants, and supplemental information, PNAS, vol. 117, No. 45, dated Nov. 10, 2020, 35 pages.

Forghani et al., Convolutional Neural Network Based Approach to In Silica Non-Anticipating Prediction of Antigenic Distance for Influenza Virus, Viruses, published Sep. 12, 2020, vol. 12, 20 pages.

Jing et al., Learning from protein structure with geometric vector perceptrons, Arxiv: 2009: 01411v2, dated Dec. 31, 2020, 18 pages.

\* cited by examiner

Side View

Dual Well

Top View

Dual Well

Heat Map Analysis of Contributions to Measured Intent

Cross talk

Background Sensors

Background Illum.

Signal Decay

Pre-phasing (ahead)

Phasing (behind)

Old results (that assumed single background level) — 1610

| 1.1-700nm | | top | left | bottom | right |
|---|---|---|---|---|---|
| 1101 | AT | 24.341909 | 19.829670 | 19.758838 | 15.628538 |
| | CT | 22.020275 | 17.317464 | 15.913662 | 15.561291 |
| 1102 | AT | 25.530696 | 19.007779 | 19.568504 | 19.609484 |
| | CT | 18.669829 | 16.893688 | 14.560277 | 19.392024 |
| 1103 | AT | 28.200664 | 18.122190 | 22.020823 | 18.537117 |
| | CT | 20.363927 | 17.324294 | 15.475405 | 19.852067 |

New results (after accounting for multiple background levels) — 1660

| 1.1-700nm | | top | left | bottom | right |
|---|---|---|---|---|---|
| 1101 | AT | 11.620936 | 12.536674 | 13.117650 | 9.950693 |
| | CT | 11.721442 | 10.781526 | 12.166851 | 8.833713 |
| 1102 | AT | 10.201675 | 12.127177 | 12.735259 | 11.259811 |
| | CT | 9.894503 | 10.465124 | 10.747423 | 10.657845 |
| 1103 | AT | 9.896417 | 11.748326 | 11.205233 | 11.560328 |
| | CT | 8.221915 | 11.101633 | 10.940892 | 8.717660 |

FIG. 16

Phasing and Prephasing Effect

SYSTEMS AND DEVICES FOR SIGNAL CORRECTIONS IN PIXEL-BASED SEQUENCING

PRIORITY APPLICATIONS

This application is a continuation of U.S. Nonprovisional patent application Ser. No. 16/874,599, titled "SYSTEMS AND DEVICES FOR CHARACTERIZATION AND PERFORMANCE ANALYSIS OF PIXEL-BASED SEQUENCING," filed May 14, 2020, which in turn claims priority to or the benefit of U.S. Provisional Patent Application No. 62/849,091, titled, "Systems and Devices for Characterization and Performance Analysis of Pixel-Based Sequencing," filed May 16, 2019; U.S. Provisional Patent Application No. 62/849,132, titled, "Base Calling using Convolutions," filed May 16, 2019; and U.S. Provisional Patent Application No. 62/849,133, titled, "Base Calling using Compact Convolutions," filed May 16, 2019. The priority applications are hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

INCORPORATIONS

The following are incorporated by reference for all purposes as if fully set forth herein:

U.S. Provisional Patent Application No. 62/821,602, titled "TRAINING DATA GENERATION FOR ARTIFICIAL INTELLIGENCE-BASED SEQUENCING,", filed on Mar. 21, 2019;

U.S. Provisional Patent Application No. 62/821,618, titled "TRAINING DATA GENERATION FOR ARTIFICIAL INTELLIGENCE-BASED SEQUENCING,", filed on Mar. 21, 2019;

U.S. Provisional Patent Application No. 62/821,681, titled "ARTIFICIAL INTELLIGENCE-BASED BASE CALLING,", filed on Mar. 21, 2019;

U.S. Provisional Patent Application No. 62/821,766, titled "ARTIFICIAL INTELLIGENCE-BASED SEQUENCING,", filed on Mar. 21, 2019;

U.S. Provisional Patent Application No. 62/821,724, titled "ARTIFICIAL INTELLIGENCE-BASED QUALITY SCORING,", filed on Mar. 21, 2019;

PCT Patent Application No. PCT/US2017/028883, titled "PHOTONIC STRUCTURE-BASED DEVICES AND COMPOSITIONS FOR USE IN LUMINESCENT IMAGING OF MULTIPLE SITES WITHIN A PIXEL, AND METHODS OF USING THE SAME," filed on Apr. 21, 2017, subsequently published as PCT Publication No. WO 2017/184997 A1, published on Oct. 26, 2017;

PCT Patent Application No. PCT/US2016/047253, titled "IN-LINE PRESSURE ACCUMULATOR AND FLOW-CONTROL SYSTEM FOR BIOLOGICAL OR CHEMICAL ASSAYS," filed on Aug. 17, 2016, subsequently published as PCT Publication No. WO 2017/034868 A1, published on Mar. 2, 2017;

PCT Patent Application No. PCT/US2017/038259, titled "SUPER-RESOLUTION MICROSCOPY," filed on Jun. 20, 2017, subsequently published as PCT Publication No. WO 2017/223041 A1, published on Dec. 28, 2017;

U.S. patent application Ser. No. 15/077,182 titled "METHODS, CARRIER ASSEMBLIES, AND SYSTEMS FOR IMAGING SAMPLES FOR BIOLOGICAL OR CHEMICAL ANALYSIS," filed on Mar. 22, 2016, subsequently published as US 2016/0281150 A1 on Sep. 29, 2016;

U.S. Pat. No. 9,193,998 B2, titled "SUPER RESOLUTION IMAGING," issued on Nov. 24, 2015;

U.S. Pat. No. 9,937,497 B2 titled "MICRODEVICES AND BIOSENSOR CARTRIDGES FOR BIOLOGICAL OR CHEMICAL ANALYSIS AND SYSTEMS AND METHODS FOR THE SAME," issued on Apr. 10, 2018;

US Publication No. US 2017/0189904 A1, titled "SYSTEMIS AND METHODS FOR BOCHEMICAL ANALYSIS INCLUDING A BASE INSTRUMENT AND A REMOVABLE CARTRIDGE," published Jul. 6, 2017;

U.S. patent application Ser. No. 15/125,124, titled "DISPOSABLE, INTEGRATED MICROFLUIDIC CARTRIDGE AND METHODS OF MAKING AND USING SAME," filed Mar. 11, 2015, subsequently published as US 2017/0016060 A1 on Jan. 19, 2017;

European Patent Application No. 08781608.8, titled "METHOD AND APPARATUS USING ELECTRIC FIELD FOR IMPROVED BIOLOGICAL ASSAYS," EP Publication No. EP 2 173 467 B1, published May 4, 2016;

U.S. patent application Ser. No. 15/067,013, titled "INTEGRATED SEQUENCING APPARATUSES AND METHODS OF USE," filed Mar. 10, 2016, subsequently patented as U.S. Pat. No. 10,167,505 B2 and issued on Jan. 1, 2019; and U.S. patent application Ser. No. 13/882,088, titled "MICRODEVICES AND BIOSENSOR CARTRIDGES FOR BIOLOGICAL OR CHEMICAL ANALYSIS AND SYSTEMS AND METHODS FOR THE SAME," filed Apr. 26, 2013, subsequently patented as U.S. Pat. No. 9,096,899 B2 and issued on Aug. 4, 2015.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Various protocols in biological or chemical research involve performing a large number of controlled reactions on local support surfaces or within predefined reaction chambers (or wells). The desired reactions may then be observed or detected and subsequent analysis may help identify or reveal properties of chemicals involved in the reaction. For example, in some multiplex assays, an unknown analyte (e.g., clusters of clonally amplified nucleic acids) having an identifiable label (e.g., fluorescent label) may be exposed to thousands of known probes under controlled conditions. Each known probe may be deposited into a corresponding well of a microplate or flow cell. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and require a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide-semiconductor (CMOS) sensor) that does not require a large optical assembly to detect the fluorescent emissions.

The proposed solid-state imaging systems will be so much different than prior optical systems that new methods and devices are required to characterize the solid-state near field imaging systems and analyze their performance. This is true both of systems that are limited to one cluster base call per sensor (or pixel) and to systems that read two or more clusters per pixel.

An opportunity arises to improve understanding of signal and noise in solid-state imaging systems, which will lead to improved designs and manufacturing processes, better quality control, and base calling technologies specifically adapted to the new systems, as they become available. The present disclosure addresses this need and provides other advantages as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The color drawings also may be available in PAIR via the Supplemental Content tab. The present disclosure, in accordance with one or more embodiments, is described in detail with reference to the following figures. The figures are provided for purposes of illustration only and merely depict example embodiments. Furthermore, it should be noted that for clarity and ease of illustration, the elements in the figures have not necessarily been drawn to scale.

FIG. 16 includes tables that illustrate reduced estimates of crosstalk after accounting for multiple background levels intrinsic to individual sensors.

DETAILED DESCRIPTION

Figure 1:
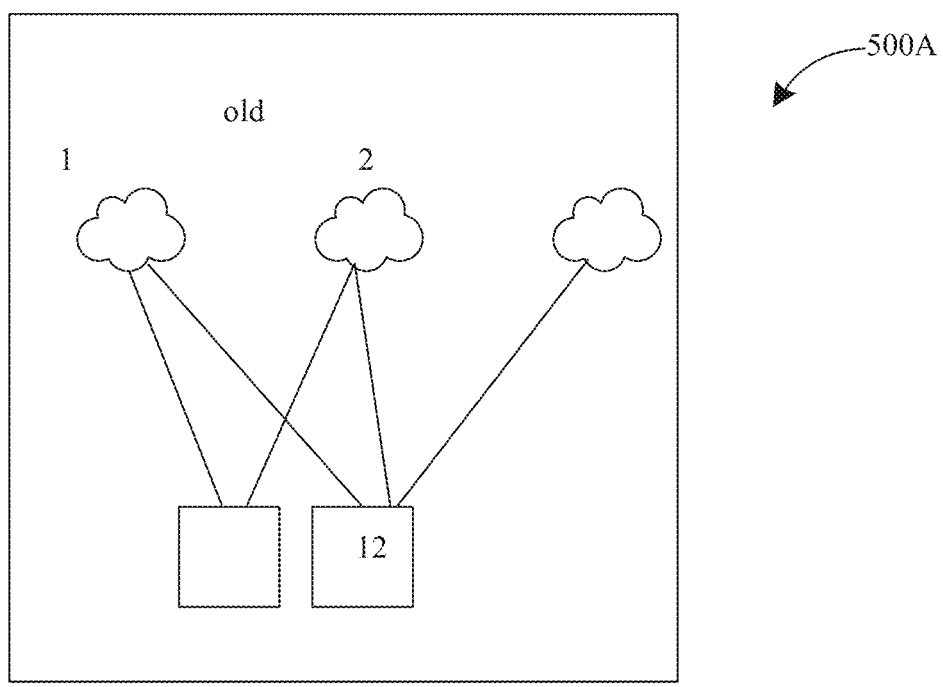
FIG. 1 shows a traditional design, in which multiple camera pixels capture a magnified image of a cluster on a substrate.

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction. For example, embodiments described herein include cartridges, biosensors, and their components as well as bioassay systems that operate with cartridges and biosensors. In particular embodiments, the cartridges and biosensors include a flow cell and one or more sensors, pixels, light detectors, or photodiodes that are coupled together in a substantially unitary structure.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" or "including" an element or a plurality of elements having a particular property may include additional elements whether or not they have that property.

As used herein, a "desired reaction" includes a change in at least one of a chemical, electrical, physical, or optical property (or quality) of an analyte-of-interest. In particular embodiments, the desired reaction is a positive binding event (e.g., incorporation of a fluorescently labeled biomolecule with the analyte-of-interest). More generally, the desired reaction may be a chemical transformation, chemical change, or chemical interaction. The desired reaction may also be a change in electrical properties. For example, the desired reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be an addition or elimination of a proton, for example, detectable as a change in pH of a surrounding solution or environment. An additional desired reaction can be detecting the flow of ions across a membrane (e.g., natural or synthetic bilayer membrane), for example as ions flow through a membrane the current is disrupted and the disruption can be detected.

In particular embodiments, the desired reaction includes the incorporation of a fluorescently-labeled molecule to an analyte. The analyte may be an oligonucleotide and the fluorescently-labeled molecule may be a nucleotide. The desired reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A desired reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term "reaction site" is a localized region where a desired reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some embodiments a reaction site may contain only a single nucleic acid molecule, for example, in a single stranded or double stranded form. Furthermore, a plurality of reaction sites may be unevenly distributed along the support surface or arranged in a predetermined manner (e.g., side-by-side in a matrix, such as in microarrays). A reaction site can also include a reaction chamber (or well) that at least partially defines a spatial region or volume configured to compartmentalize the desired reaction.

This application uses the terms "reaction chamber" and "well" interchangeably. As used herein, the term "reaction chamber" or "well" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some embodiments, sensors (e.g., light detectors, photodiodes) are associated with corresponding pixel areas of a sample surface of a biosensor. As such, a pixel area is a geometrical construct that represents an area on the biosensor's sample surface for one sensor (or pixel). A sensor that is associated with a pixel area detects light emissions gathered from the associated pixel area when a desired reaction has occurred at a reaction site or a reaction chamber overlying the associated pixel area. In a flat surface embodiment, the pixel areas can overlap. In some cases, a plurality of sensors may be associated with a single reaction site or a single reaction chamber. In other cases, a single sensor may be associated with a group of reaction sites or a group of reaction chambers.

As used herein, a "biosensor" includes a structure having a plurality of reaction sites and/or reaction chambers (or wells). A biosensor may include a solid-state imaging device (e.g., CCD or CMOS imager) and, optionally, a flow cell mounted thereto. The flow cell may include at least one flow channel that is in fluid communication with the reaction sites and/or the reaction chambers. As one specific example, the biosensor is configured to fluidically and electrically couple to a bioassay system. The bioassay system may deliver reactants to the reaction sites and/or the reaction chambers according to a predetermined protocol (e.g., sequencing-by-synthesis) and perform a plurality of imaging events. For example, the bioassay system may direct solutions to flow along the reaction sites and/or the reaction chambers. At least one of the solutions may include four types of nucleotides having the same or different fluorescent labels. The nucleotides may bind to corresponding oligonucleotides located at the reaction sites and/or the reaction chambers. The bioassay system may then illuminate the reaction sites and/or the reaction chambers using an excitation light source (e.g., solid-state light sources, such as light-emitting diodes or LEDs). The excitation light may have a predetermined wavelength or wavelengths, including a range of wavelengths. The excited fluorescent labels provide emission signals that may be captured by the sensors.

In alternative embodiments, the biosensor may include electrodes or other types of sensors configured to detect other identifiable properties. For example, the sensors may be configured to detect a change in ion concentration. In another example, the sensors may be configured to detect the ion current flow across a membrane.

As used herein, a "cluster" is a colony of similar or identical molecules or nucleotide sequences or DNA strands. For example, a cluster can be an amplified oligonucleotide or any other group of a polynucleotide or polypeptide with a same or similar sequence. In other embodiments, a cluster can be any element or group of elements that occupy a physical area on a sample surface. In embodiments, clusters are immobilized to a reaction site and/or a reaction chamber during a base calling cycle.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference.

In some embodiments, nucleic acids can be attached to a surface and amplified using bridge amplification. Useful bridge amplification methods are described, for example, in U.S. Pat. No. 5,641,658; WO 2007/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached).

By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

In particular embodiments, the assay protocols executed by the systems and methods described herein include the use of natural nucleotides and also enzymes that are configured to interact with the natural nucleotides. Natural nucleotides include, for example, ribonucleotides (RNA) or deoxyribonucleotides (DNA). Natural nucleotides can be in the mono-, di-, or tri-phosphate form and can have a base selected from adenine (A), thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In embodiments that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publication Nos. 2008/0242560 A1 or 2008/0234136 A1, each of which is incorporated herein in its entirety. A substance that is held or disposed in a reaction chamber can be in a solid, liquid, or gaseous state.

As used herein, "base calling" identifies a nucleotide base in a nucleic acid sequence. Base calling refers to the process of determining a base call (A, C, G, T) for every cluster at a specific cycle. As an example, base calling can be performed utilizing four-channel, two-channel or one-channel methods and systems described in the incorporated materials of U.S. Patent Application Publication No. 2013/0079232. In particular embodiments, a base calling cycle is referred to as a "sampling event." In one dye and two-channel sequencing protocol, a sampling event comprises two illumination stages in time sequence, such that a pixel signal is generated at each stage. The first illumination stage induces illumination from a given cluster indicating nucleotide bases A and T in a AT pixel signal, and the second illumination stage induces illumination from a given cluster indicating nucleotide bases C and T in a CT pixel signal.

Introduction

A new approach to flow cell design involves nano wells in which one or two clusters are amplified. FIG. 1 shows a traditional design, in which multiple camera pixels capture a magnified image of a cluster on a substrate. In one design, a nano well is built on top of a CMOS sensor substrate. See application Ser. No. 16/241,905. In another design, a sensor is positioned directly over the nano well. In both designs, a sampling device includes a sample surface having an array of pixel areas and a solid-state array of sensors. Each sensor generates pixel signals in base calling cycles. The pixel signals represent light gathered from a corresponding pixel area of the sample surface. In some implementations, a sensor collects light from two wells. In other implementations, off axis illumination can distinguish signals from two clusters growing in one well. This is much different from prior camera-reliant, far field imaging approaches.

Fluidic channels carry reagents over and through the nano wells during sequencing. In each cycle, light energy, such as laser illumination, stimulates fluorescent tags attached to sequences to glow, signaling the current nucleotide in the sequence. Light from the tags is collected by the sensors. Using alternative chemistries, one, two or four illuminations produce an equal number of intensity maps. These are near field intensity maps, as distinct from photographic images, more like sensing a pen stroke than taking a picture.

An opportunity arises to characterize response of the tags to stimulation, to analyze performance of the new designs. Results of characterization guide cell design, manufacturing and operation. Results of characterization also can be applied to improve base calling.

Flow cells with one sensor per well are a relatively new design for parallel sequencing of millions of amplified clusters. Rapid development and future advances in technology are inevitable, as sequencing has advanced rapidly, with computational improvements and cost reductions at rates following Moore's law. Each new design needs to be characterized and analyzed for performance.

Consider part of a massively parallel design including a patch of nine CMOS sensors overlaid by filters and nano wells. The nano wells are sized to accommodate amplification and growth of one or two clusters (FIGS. 2, 3A-B) or alternatively to hold a micro bead on which a sequence is synthesized. Suppose that in each cycle of synthesis, the nano wells are illuminated by a red laser and then a green laser. Fluorescence of tags in clusters in the nano wells are collected by the CMOS sensors in red and green channels. Suppose the synthesis proceeds and calls bases for 150 cycles.

Development of the technology disclosed began with physical analysis of contributions to sensed intensity. Analysis revealed that, as sequencing proceeds, accurate base calling becomes increasingly difficult, because signal strength decreases and noise increases (FIG. 4), resulting in a substantially decreased signal-to-noise ratio. Physically, it was observed that later synthesis steps attach tags in a different position relative to the sensor than earlier synthesis steps. When the sensor is below a sequence that is being synthesized, signal decay results from attaching tags to strands (206A) further away from the sensor (206) in later sequencing steps than in earlier steps. We refer to this as signal decay. In some designs, where the sensor is above the substrate that holds cluster, signal could increase, instead of decay, as sequencing proceeds.

In the flow cell design investigated, while the signal decays, noise grows. Physically, phasing and pre-phasing (505) increase noise as sequencing proceeds. Phasing refers to steps in sequencing in which tags fail to advance along the sequence. Pre-phasing refers to sequencing steps in which tags jump two positions forward instead of one, during a sequencing cycle. Phasing and pre-phasing are both relatively infrequent (FIG. 10, phasing kernel), on the order of once in 500 to 1000 cycles. Phasing is slightly more frequent than pre-phasing. Phasing and pre-phasing impact individual strands in a cluster that is producing intensity data, so the intensity noise distribution from a cluster accumulates in a binomial, trinomial, quadranomial, etc. expansion (513) as sequencing proceeds. Graphically, this is depicted as a widening distribution cone (517) of sequencing progress among strands in a cluster as sequencing proceeds.

Figure 13C:
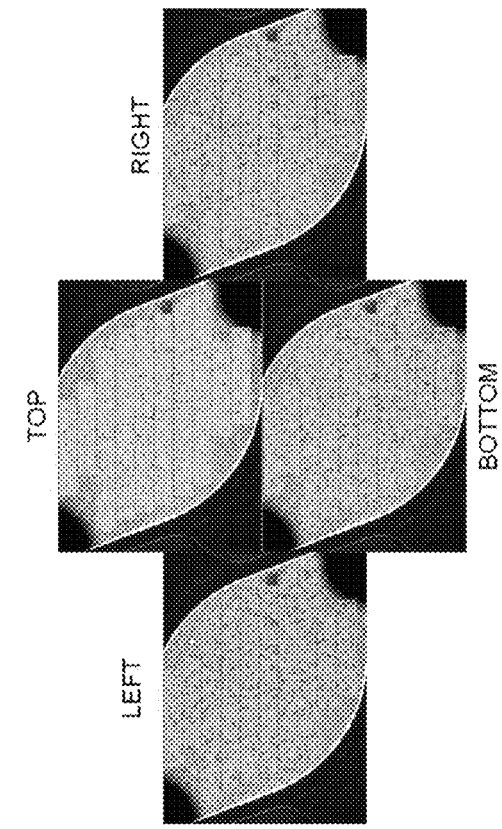
FIGS. 13A-13F are a series of heat maps created by applying false color to a photograph of a flow cell, based on analysis of contributions of various factors to measured intensities in an intensity map for one channel.

Two additional sources contribute to sensor readouts of intensity. See, FIG. 13. They are cross talk and background. In a patch of nine sensors, the middle sensor receives crosstalk noise from at least four adjoining nano wells to the north, south, east and west (top, bottom, left and right) of center. Square or nearly square pixels in the checkerboard pattern receive more crosstalk from the primary points of the compass than from the diagonals. Investigation revealed that crosstalk is not symmetrical. FIG. 13C. Contributions to asymmetry appear to relate to the manufacturing of flow cells and positioning of the illumination source. Cross talk is a factor of intensity measured in the adjoining cells, which varies between cycles, because cross talk is the portion of the signal from the adjoining cells that leaks into the middle cell.

Figure 14B:
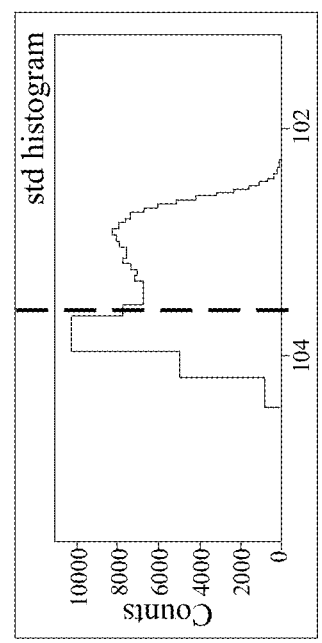
FIGS. 14A-14B reflect sensor-specific variation in background readings that is not randomly distributed.
Figure 14A:
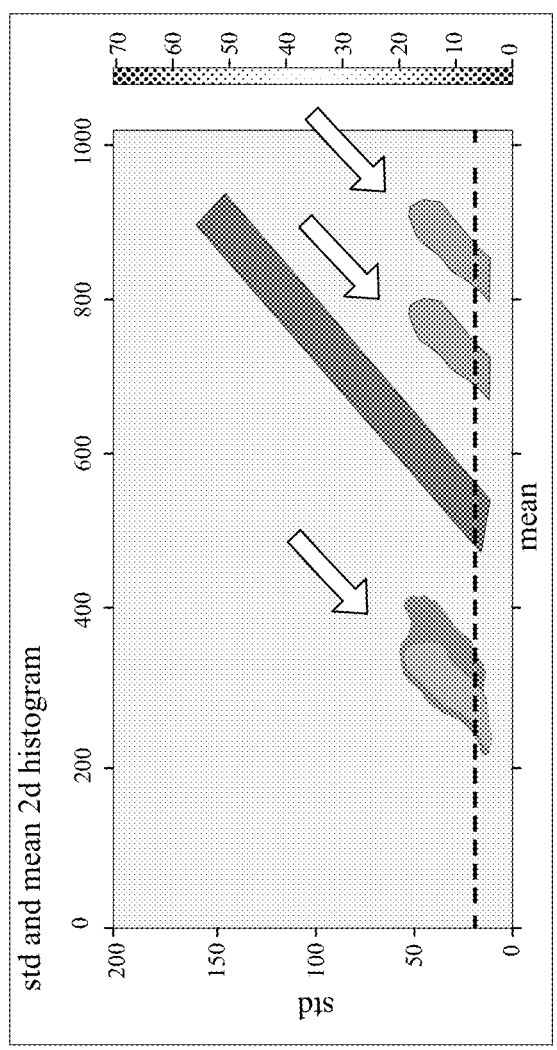
Figure 15:
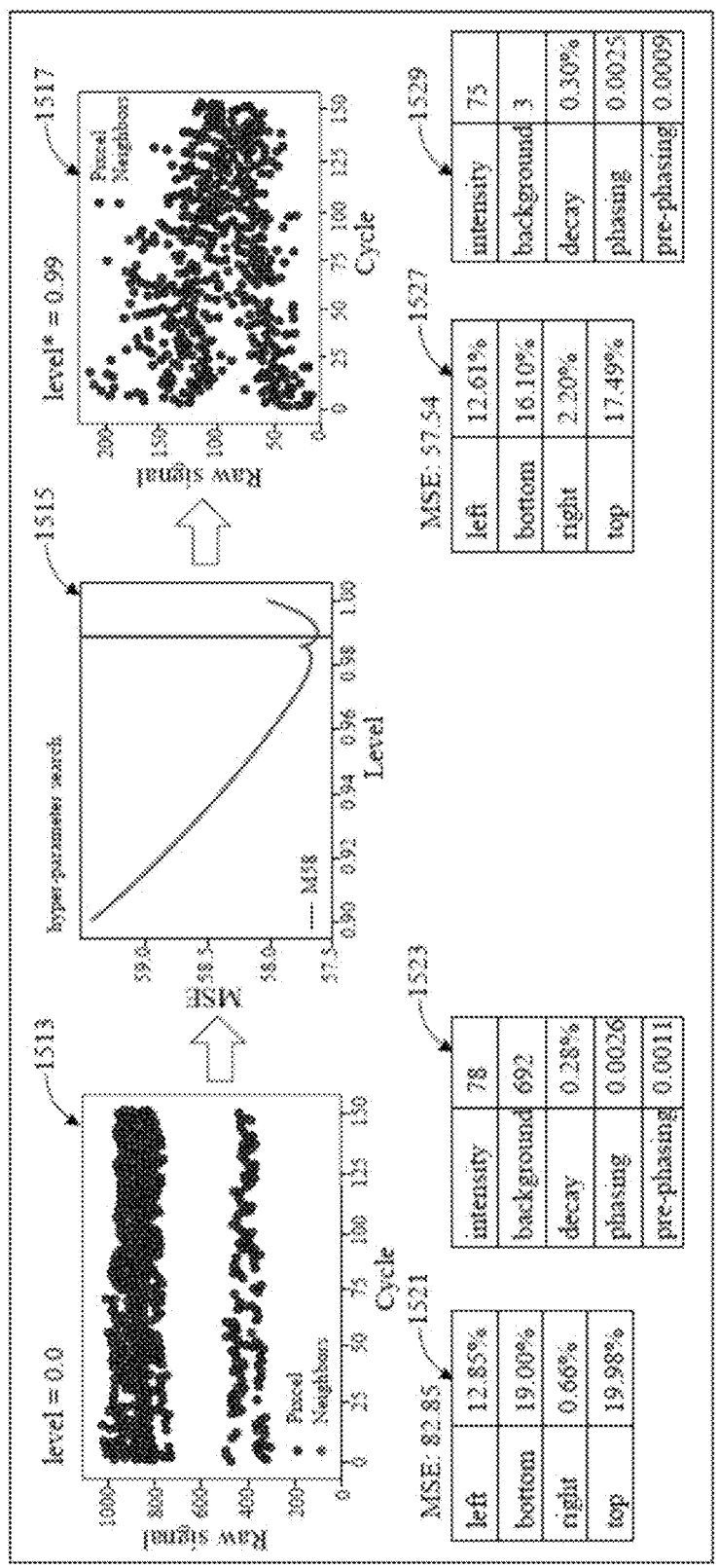
FIG. 15 presents a background level hyper-parameter approach to setting a particular pixel's background level taking into account background levels of its neighbors.
Figure 17:
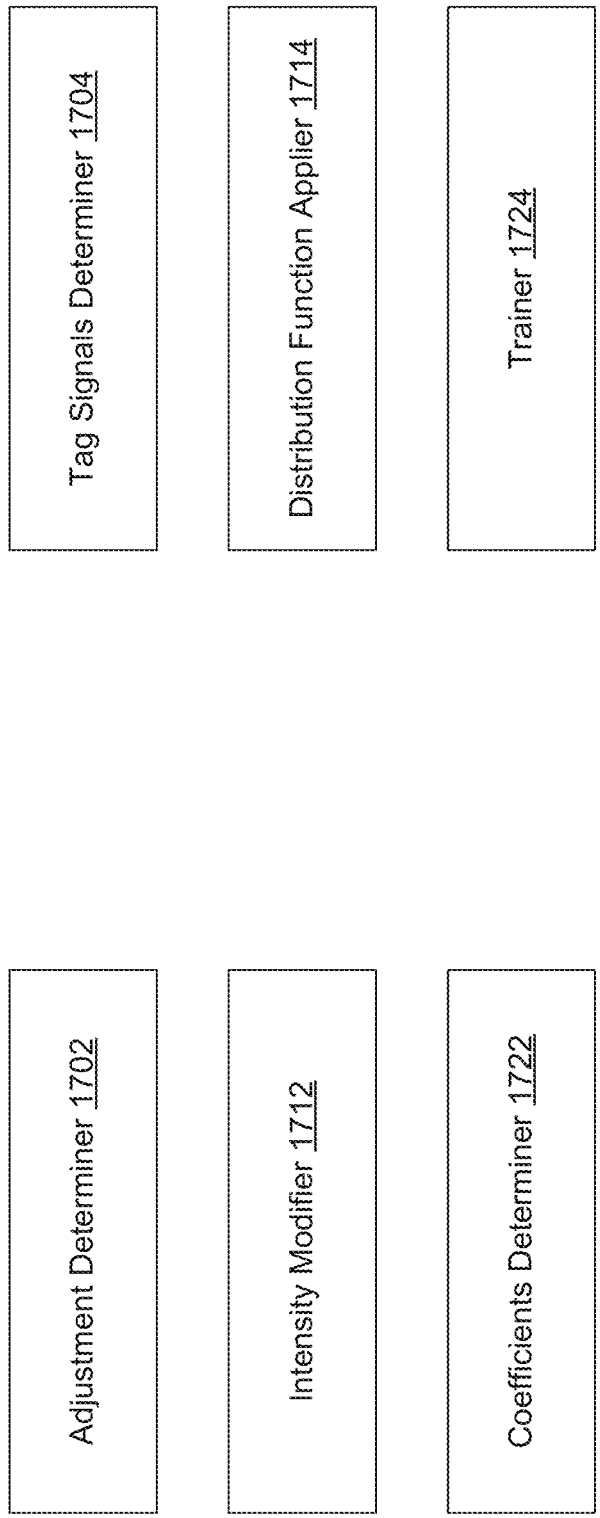
FIG. 17 shows various modules that implement the technology disclosed.

Background intensity of a particular cell is relatively steady between cycles, but varies across the sensors. FIG. 14A-B. Positioning of the illumination source, which can vary by illumination color, creates a spatial pattern of background variation over a field of the sensors. FIG. 13A. Surprisingly, manufacturing differences among the sensors were observed to produce different background intensity readouts, even between adjoining sensors. FIG. 15. In a first approximation, idiosyncratic variation among sensors can be ignored. In a refinement, the idiosyncratic variation in background intensity among sensors can be taken into account, with the surprising improvement in estimation of crosstalk effects. FIG. 16.

In one model, background intensity is a constant parameter to be fit, either overall or per pixel. In the refinement, different background intensities are taken into account when estimating crosstalk. FIGS. 14A-B, 15. Using background intensity applicable to sensors in a patch of nine, for instance, an improvement in mean squared error is achieved and cross talk estimations become more realistic, decreasing by half in some directions and increasing above negligible in others. FIG. 16.

An equation that approximates relationships among contributors to measured intensity is:

$$\mathcal{Y} =_{d\circ} \mathcal{SW}_{u+} \mathcal{H}_{c+} \mathcal{b}, \text{ wherein}$$

$\mathcal{Y}$ is a vector of measured intensities for a measurement channel over n cycles (e.g., 150), such as from a middle sensor in a patch of 9, c is a vector of measured intensities over n cycles from sensors north, south, east and west of the middle sensor, u is a Boolean vector indicating an active signal, over n cycles, which indicates whether a tag that is in correct time (not phasing or pre-phasing) emits a signal for the particular intensity measurement channel, which derives from base calling, d is an estimated decay (or increase) vector for a decreasing proportion of tag florescence that a sensor measures over the n cycles, which reduces the signal, $\mathcal{W}$ is an estimated matrix of signal distributions, over phasing (behind), in correct time, and pre-phasing (ahead) tag fluorescence, over the n cycles, which is an increasing part of the noise that grows over cycles, $\mathcal{H}$ is an estimated matrix of cross-talk contributions to measured intensity $\mathcal{Y}$ of the middle sensor that spills over from measured intensities e of the sensors north, south, east and west of the middle sensor, which is a varying part of the noise that is a factor of measured adjoining intensities, $\mathcal{b}$ is an estimated background intensity contribution to measured intensity $\mathcal{Y}$, which is a steady part of the noise, which may be individualized to the middle pixel, spatially and/or idiosyncratically, and $\mathcal{s}$ is a derived signal emanating from one or two clusters in a nano well measured by the middle cell, the signal. Solving for $\mathcal{s}$:

$$\frac{\mathcal{Y} - \mathcal{H} c - \mathcal{b}}{d \circ \mathcal{W} u} = \mathcal{s}$$

Does this work? What are the rules for rearranging the dot product in a solution?

This equation is for illustration purposes because, as described above, estimation of cross-talk can depend on idiosyncratic variations in background measurements between adjoining sensors. The equation applies separately to each intensity measurement channel, though estimated parameter values may be similar. The same characterization approach could be applied to an overhead sensor, as opposed to a substrate sensor, with the decay vector liable to become an increase vector, as florescent tagging approaches the sensor.

Base Calling System

The technology disclosed for use with an advanced system (653, 673) is generally applicable to base calling systems such as depicted in FIG. 1 of U.S. Nonprovisional patent application Ser. No. 16/241,902, referenced above.

Biosensor

Figure 2:
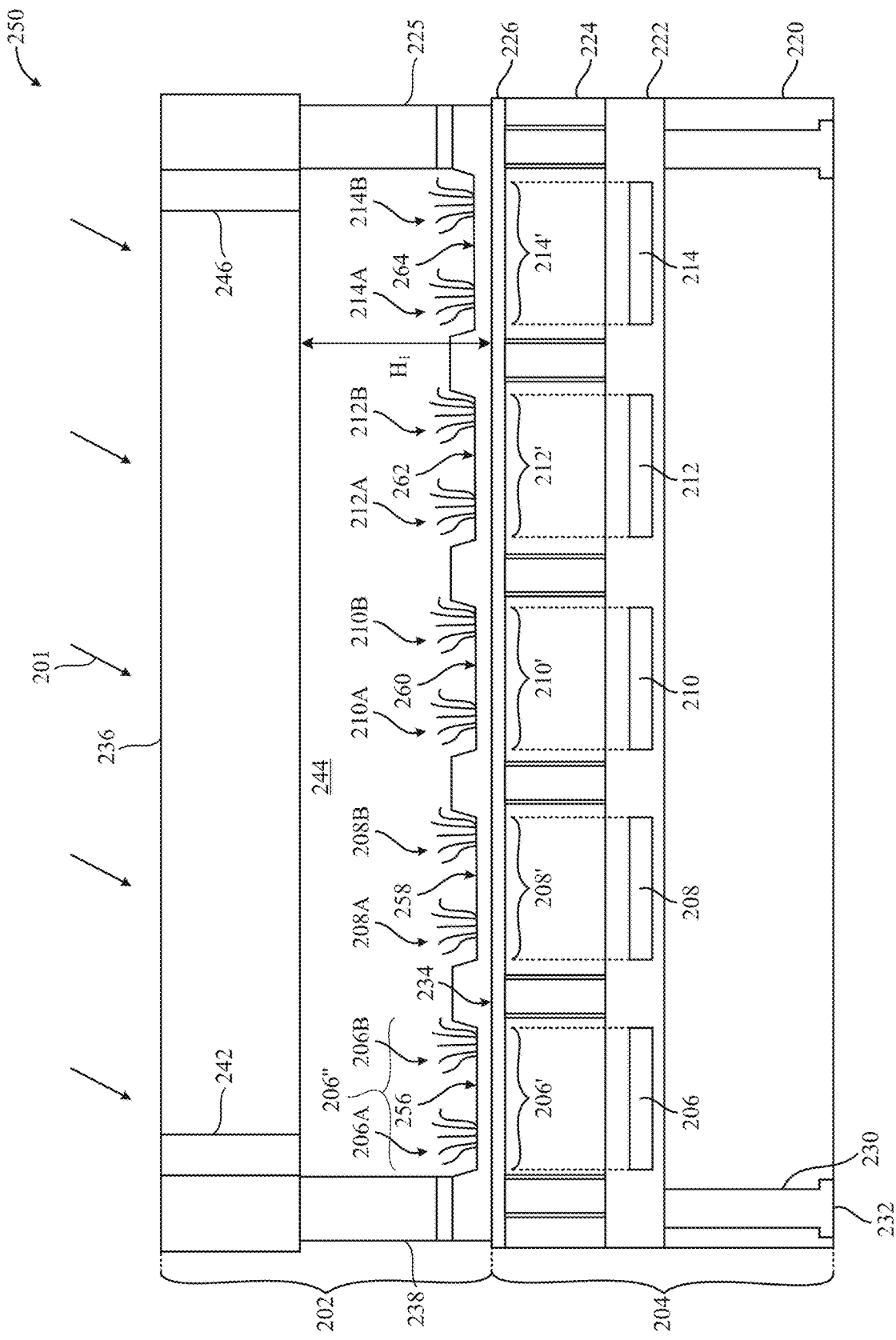
FIG. 2 illustrates a cross-section of a biosensor that can be used in various embodiments.

FIG. 2 illustrates a cross-section of a biosensor 200 that can be used in various embodiments. Biosensor 200 has pixel areas 206', 208', 210', 212', and 214' that can each hold more than one cluster during a base calling cycle (e.g., 2 clusters per pixel area). As shown, the biosensor 200 may include a flow cell 202 that is mounted onto a sampling device 204. In the illustrated embodiment, the flow cell 202 is affixed directly to the sampling device 204. However, in alternative embodiments, the flow cell 202 may be removably coupled to the sampling device 204. The sampling device 204 has a sample surface 234 that may be functionalized (e.g., chemically or physically modified in a suitable manner for conducting the desired reactions). For example, the sample surface 234 may be functionalized and may include a plurality of pixel areas 206', 208', 210', 212', and 214' that can each hold more than one cluster during a base calling cycle (e.g., each having a corresponding cluster pair 206AB, 208AB, 210AB, 212AB, and 214AB immobilized thereto). Each pixel area is associated with a corresponding sensor (or pixel or photodiode) 206, 208, 210, 212, and 214, such that light received by the pixel area is captured by the corresponding sensor. A pixel area 206' can be also associated with a corresponding reaction site 206" on the sample surface 234 that holds a cluster pair, such that light emitted from the reaction site 206" is received by the pixel area 206' and captured by the corresponding sensor 206. As a result of this sensing structure, in the case in which two or more clusters are present in a pixel area of a particular sensor during a base calling cycle (e.g., each having a corresponding cluster pair), the pixel signal in that base calling cycle carries information based on all of the two or more clusters. As a result, signal processing as described herein is used to distinguish each cluster, where there are more clusters than pixel signals in a given sampling event of a particular base calling cycle.

In the illustrated embodiment, the flow cell 202 includes sidewalls 238, 240 and a flow cover 236 that is supported by the sidewalls 238, 240. The sidewalls 238, 240 are coupled to the sample surface 234 and extend between the flow cover 236 and the sidewalls 238, 240. In some embodiments, the sidewalls 238, 240 are formed from a curable adhesive layer that bonds the flow cover 236 to the sampling device 204.

The sidewalls 238, 240 are sized and shaped so that a flow channel 244 exists between the flow cover 236 and the sampling device 204. As shown, the flow channel 244 may include a height $H_1$ that is determined by the sidewalls 238, 240. The height $H_1$ may be between about 50-400 μm (micrometer) or, more particularly, about 80-200 μm. In the illustrated embodiment, the height $H_1$ is about 100 μm. The flow cover 236 may include a material that is transparent to excitation light 201 propagating from an exterior of the biosensor 200 into the flow channel 244. As shown in FIG. 2, the excitation light 201 approaches the flow cover 236 at a non-orthogonal angle. However, this is only for illustrative purposes as the excitation light 201 may approach the flow cover 236 from different angles.

Also shown, the flow cover 236 may include inlet and outlet ports 242, 246 that are configured to fluidically engage other ports (not shown). For example, the other ports may be from the cartridge or the workstation. The flow channel 244 is sized and shaped to direct a fluid along the sample surface 234. The height $H_1$ and other dimensions of the flow channel 244 may be configured to maintain a substantially even flow of a fluid along the sample surface 234. The dimensions of the flow channel 244 may also be configured to control bubble formation.

As shown in the example of FIG. 2, the sidewalls 238, 240 and the flow cover 236 are separate components that are coupled to each other. In alternative embodiments, the sidewalls 238, 240 and the flow cover 236 may be integrally formed such that the sidewalls 238, 240 and the flow cover 236 are formed from a continuous piece of material. By way of example, the flow cover 236 (or the flow cell 202) may comprise a transparent material, such as glass or plastic. The flow cover 236 may constitute a substantially rectangular block having a planar exterior surface and a planar inner surface that defines the flow channel 244. The block may be mounted onto the sidewalls 238, 240. Alternatively, the flow cell 202 may be etched to define the flow cover 236 and the sidewalls 238, 240. For example, a recess may be etched into the transparent material. When the etched material is mounted to the sampling device 204, the recess may become the flow channel 244.

The sampling device 204 may be similar to, for example, an integrated circuit comprising a plurality of stacked substrate layers 220-226. The substrate layers 220-226 may include a base substrate 220, a solid-state imager 222 (e.g., CMOS image sensor), a filter or light-management layer 224, and a passivation layer 226. It should be noted that the above is only illustrative and that other embodiments may include fewer or additional layers. Moreover, each of the substrate layers 220-226 may include a plurality of sublayers. As will be described in greater detail below, the sampling device 204 may be manufactured using processes that are similar to those used in manufacturing integrated circuits, such as CMOS image sensors and CCDs. For example, the substrate layers 220-226 or portions thereof may be grown, deposited, etched, and the like to form the sampling device 204.

The passivation layer 226 is configured to shield the filter layer 224 from the fluidic environment of the flow channel 244. In some cases, the passivation layer 226 is also configured to provide a solid surface (i.e., the sample surface 234) that permits biomolecules or other analytes-of-interest to be immobilized thereon. For example, each of the reaction sites may include a cluster of biomolecules that are immobilized to the sample surface 234. Thus, the passivation layer 226 may be formed from a material that permits the reaction sites to be immobilized thereto. The passivation layer 226 may also comprise a material that is at least transparent to a desired fluorescent light. By way of example, the passivation layer 226 may include silicon nitride (Si2N4) and/or silica (SiO2). However, other suitable material(s) may be used. In the illustrated embodiment, the passivation layer 226 may be substantially planar. However, in alternative embodiments, the passivation layer 226 may include recesses, such as pits, wells, grooves, and the like. In the illustrated embodiment, the passivation layer 226 has a thickness that is about 150-200 nm and, more particularly, about 170 nm.

The filter layer 224 may include various features that affect the transmission of light. In some embodiments, the filter layer 224 can perform multiple functions. For instance, the filter layer 224 may be configured to (a) filter unwanted light signals, such as light signals from an excitation light source; (b) direct emission signals from the reaction sites toward corresponding sensors 206, 208, 210, 212, and 214 that are configured to detect the emission signals from the reaction sites; or (c) block or prevent detection of unwanted emission signals from adjacent reaction sites. As such, the filter layer 224 may also be referred to as a light-management layer. In the illustrated embodiment, the filter layer 224 has a thickness that is about 1-5 μm and, more particularly, about 2-4 μm. In alternative embodiments, the filter layer 224 may include an array of microlenses or other optical components. Each of the microlenses may be configured to direct emission signals from an associated reaction site to a sensor.

In some embodiments, the solid-state imager 222 and the base substrate 220 may be provided together as a previously constructed solid-state imaging device (e.g., CMOS chip). For example, the base substrate 220 may be a wafer of silicon and the solid-state imager 222 may be mounted thereon. The solid-state imager 222 includes a layer of semiconductor material (e.g., silicon) and the sensors 206, 208, 210, 212, and 214. In the illustrated embodiment, the sensors are photodiodes configured to detect light. In other embodiments, the sensors comprise light detectors. The solid-state imager 222 may be manufactured as a single chip through a CMOS-based fabrication processes.

The solid-state imager 222 may include a dense array of sensors 206, 208, 210, 212, and 214 that are configured to detect activity indicative of a desired reaction from within or along the flow channel 244. In some embodiments, each sensor has a pixel area (or detection area) that is about 1-2 square micrometer ($\mu m^2$). The array can include 500,000 sensors, 5 million sensors, 10 million sensors, or even 120 million sensors. The sensors 206, 208, 210, 212, and 214 can be configured to detect a predetermined wavelength of light that is indicative of the desired reactions.

In some embodiments, the sampling device 204 includes a microcircuit arrangement, such as the microcircuit arrangement described in U.S. Pat. No. 7,595,882, which is incorporated herein by reference in the entirety. More specifically, the sampling device 204 may comprise an integrated circuit having a planar array of the sensors 206, 208, 210, 212, and 214. The array of the sensors 206, 208, 210, 212, and 214 can be communicatively coupled to a row decoder and a column amplifier or decoder. The column amplifier can also be communicatively coupled to a column analog-to-digital converter (Column ADC/Mux). Other circuitry may be coupled to the above components, including a digital signal processor and memory. Circuitry formed within the sampling device 204 may be configured for at least one of signal amplification, digitization, storage, and processing. The circuitry may collect and analyze the detected fluorescent light and generate pixel signals (or detection signals) for communicating detection data to the signal processor 128. The circuitry may also perform additional analog and/or digital signal processing in the sampling device 204. Sampling device 204 may include conductive vias 230 that perform signal routing (e.g., transmit the pixel signals to the signal processor 128). The pixel signals may also be transmitted through electrical contacts 232 of the sampling device 204.

However, the sampling device 204 is not limited to the above constructions or uses as described above. In alternative embodiments, the sampling device 204 may take other forms. For example, the sampling device 204 may comprise a CCD device, such as a CCD camera, that is coupled to a flow cell or is moved to interface with a flow cell having reaction sites therein. In other embodiments, the sampling device 204 may be a CMOS-fabricated sensor, including chemically sensitive field effect transistors (chemFET), ion-sensitive field effect transistors (ISFET), and/or metal oxide semiconductor field effect transistors (MOSFET). Such embodiments may include an array of field effect transistors (FET's) that may be configured to detect a change in electrical properties within the reaction chambers. For example, the FET's may detect at least one of a presence and concentration change of various analytes. By way of example, the array of FET's may monitor changes in hydrogen ion concentration. Such sampling devices are described in greater detail is U.S. Patent Application Publication No. 2009/0127589, which is incorporated by reference in the entirety for the use of understanding such FET arrays.

FIG. 2 further shows a cross-section of a biosensor 250 that can be used in various embodiments. Biosensor 250 has wells 256, 258, 260, 262, and 264 that can each hold more than one cluster during a base calling cycle (e.g., 2 clusters per well). The sample surface 234 may be substantially planar (not shown.) In the embodiment shown, the sample surface 234 is shaped to define wells (or reaction chambers) in which each well has one or more reaction sites. The wells may be defined by, for example, well walls that effectively separate the reaction site(s) of one well from the reaction site(s) of an adjacent well.

As shown in FIG. 2, the wells 256, 258, 260, 262, and 264 may be distributed in a pattern along the sample surface 234. For example, the wells 256, 258, 260, 262, and 264 may be located in rows and columns along the sample surface 234 in a manner that is similar to a microarray. However, it is understood that various patterns of wells 256, 258, 260, 262, and 264 may be used. In particular embodiments, each of the wells 256, 258, 260, 262, and 264 includes more than one cluster of biomolecules (e.g., oligonucleotides) that are immobilized on the sample surface 234. For example, well 256 holds cluster pair 206AB, well 258 holds cluster pair 208AB, well 260 holds cluster pair 210AB, well 262 holds cluster pair 212AB, and well 264 holds cluster pair 214AB.

The sensors are configured to detect light signals that are emitted from within the wells. In particular embodiments, pixel areas 206', 208', 210', 212', and 214' can be also associated with corresponding wells 256, 258, 260, 262, and 264 on the sample surface 234, such that light emitted from the wells 256, 258, 260, 262, and 264 is received by the associated pixel areas 206', 208', 210', 212', and 214' and captured by the corresponding sensors 206, 208, 210, 212, and 214.

In embodiments, the sample surface 234 has a fixed position relative to the sampling device 204 so that the wells 256, 258, 260, 262, and 264 have known spatial locations relative to at least one predetermined sensor (or pixel). The at least one predetermined sensor detects activity of the desired reactions from the overlying well. As such, the wells 256, 258, 260, 262, and 264 may be assigned to at least one of the sensors 206, 208, 210, 212, and 214. To this end, the circuitry of the sampling device 204 may include kernels that automatically associate pixel signals (or detection signals) provided by predetermined sensors 206, 208, 210, 212, and 214 with the assigned wells 256, 258, 260, 262, and 264. By way of example, when pixel signals are generated by sensor 206, the pixel signals will automatically be associated with the well 256. Such a configuration may facilitate processing and analyzing the detection data. For instance, the pixel signals from one well may automatically be located at a certain position on the array based on row-wise and/or column-wise decoding.

In some embodiments, the sensors (or pixels) are underlying or below the clusters. In other embodiments, the sensors (or pixels) are overlying or on top of the clusters. In yet other embodiments, the sensors (or pixels) are to the side of the clusters (e.g., to the right and/or left).

Multiple Cluster Base Call Per Sensor (or Pixel)

In embodiments, the technology disclosed increases throughput of the biosensor 205 by using pixel signals from fewer sensors (or pixels) than a number of clusters base called in a base calling cycle. In particular embodiments, if the biosensor 200 has N active sensors, then the technology disclosed uses pixel signals from the N active sensors to base call N+M clusters, where M is a positive integer. In embodiments, this is achieved by base calling multiple clusters per sensor (or pixel), as described below.

In embodiments, a sensor (or pixel) on the sample surface 234 is configured to receive light emissions from at least two clusters. In some embodiments, the sensor simultaneously receives the light emissions from the at least two clusters.

In particular embodiments, the intensity of respective light emissions of the two clusters is significantly different such that one of the two clusters is a "bright" cluster and the other is a "dim" cluster. In embodiments, the intensity values vary between base calling cycles and thus the classification of bright and dim can also change between cycles. In other embodiments, a bright cluster is referred to as a "major" or "dominant" cluster and a dim cluster is referred to as a "minor" or "subordinate" cluster. Some examples of intensity value ratios of emissions between bright and dim clusters include 0.55:0.45, 0.60:0.25, 0.65:0.25, 0.70:0.20, 0.75:0.25, 0.80:0.20, 0.85:0.15, 0.90:0.10, and 0.95:0.05.

In yet other embodiments, the at least two clusters are not bright and dim clusters, but instead clusters with different intensities or clusters generating different types of signals.

During each sampling event (e.g., each illumination stage or each image acquisition stage), a signal processor receives a common, single pixel signal for at least two clusters (e.g., both the bright and dim clusters). The common, single pixel generated at each sampling event includes/represents/reflects/carries light emissions/intensity signals/light captured/sensed information for or from the at least two clusters (e.g., both the bright and dim clusters). In other words, the at least two clusters (e.g., both the bright and dim clusters) contribute to the common, single pixel generated at each sampling event. Accordingly, light emissions from the at least two clusters (e.g., both the bright and dim clusters) are detected simultaneously at each sampling event and the common, single pixel reflects light emissions from the at least two clusters (e.g., both the bright and dim clusters).

For example, in FIG. 2, cluster pair 206AB includes two clusters 206A and 206B which share a sensor 206. As such, cluster 206A can be the dim cluster and cluster 206B can be the bright cluster, depending on their respective intensity values. The signal processor then uses a base calling algorithm to classify pixel signals from the bright and dim clusters into one of sixteen distributions, as described below. In particular embodiments, the bright and dim cluster co-occupy a well, such as well 206. Thus, cluster pairing can be defined based on a shared pixel area or a shared well, or both.

Dual Wells Per Sensor (or Pixel)

Figure 3A:
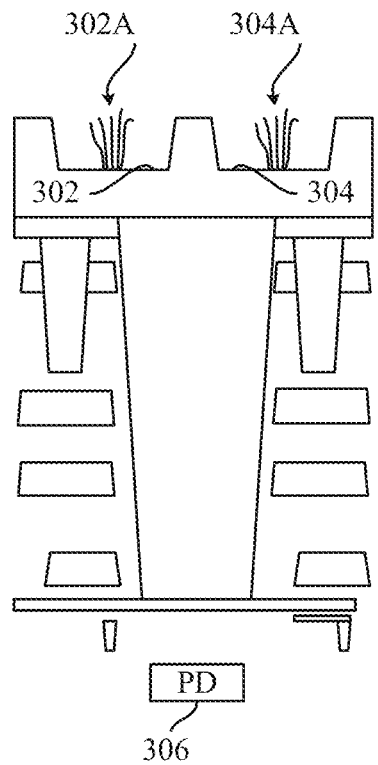
FIG. 3A illustrates a side view of a sample surface having two wells per pixel area including a dominant (or major) well and a subordinate (or minor) well in accordance with one embodiment.
Figure 3B:
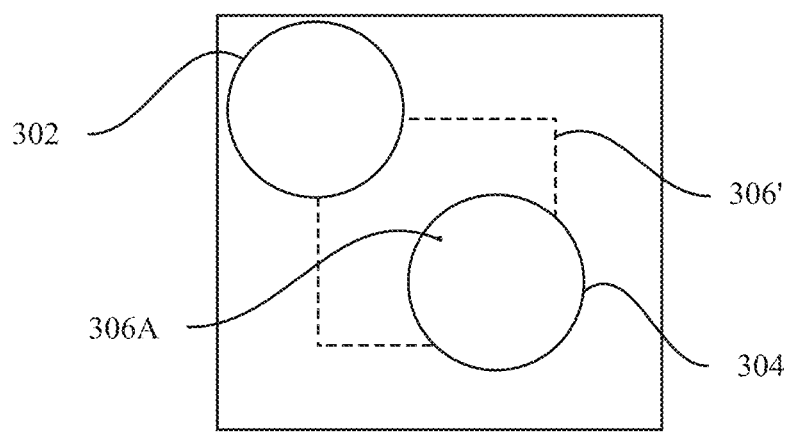
FIG. 3B depicts a top plan view of the sample surface.

FIG. 3A illustrates a side view 300A of a sample surface having two wells per pixel area including a dominant (or major) well and a subordinate (or minor) well in accordance with one embodiment. FIG. 3B depicts a top plan view 300B of the sample surface of FIG. 3A.

In the illustrated embodiment, shared sensor 306 (or pixel) corresponds to two wells 302 and 304 on the sample surface 234. The dominant well has a larger cross section over the pixel area than the subordinate well. Well 304 is the dominant well and well 302 is the subordinate well because well 304 has a larger cross section over the sensor 306.

In embodiments, the two wells have different offsets relative to a center of the pixel area 306'. In the illustrated embodiment, dominant well 304 is more proximate to the pixel area center 306A than the subordinate well 302 (i.e., dominant well 304 has a smaller offset relative to the pixel area center 306A than the subordinate well 302).

Due to the differential cross section coverage and relative offsets result, the sensor 306 receives different amounts of illumination from the two wells during illumination stages of the base calling cycle (or sampling event). Since each of the wells 302 and 304 holds a corresponding cluster 302A and 304A, the different amounts of illumination allow for identification of one of the clusters as bright (or major) and the other as dim (or minor). In the illustrated embodiment, cluster 302A within the dominant well 302 is identified as the bright cluster and cluster 304A within the subordinate well 304 is identified as the dim cluster. In embodiments, sensor 306 receives an amount of illumination from the bright cluster 302A that is greater than an amount of illumination received from the dim cluster 304A in the subordinate well 304.

After the bright and dim clusters are identified, they can be base called by the signal processor 138 using one of the sequencing protocols discussed above. In some dual well per sensor (or pixel) embodiments, the technology disclosed increases throughput of the biosensor 300 by base calling two clusters 302A and 302B held by two corresponding wells 302 and 304 using one shared sensor 306. In other dual well per sensor (or pixel) embodiments, the technology disclosed increases throughput of the biosensor 300 by using N sensors to base call N+M clusters on corresponding N+M wells of the sample surface 234, where M is a positive integer. In some embodiments, M is equal to N or almost equal to N. In other embodiments, M might not be equal to N or even be less than N.

Addressing the Decreasing Signal to Noise Ratio

Figure 4:
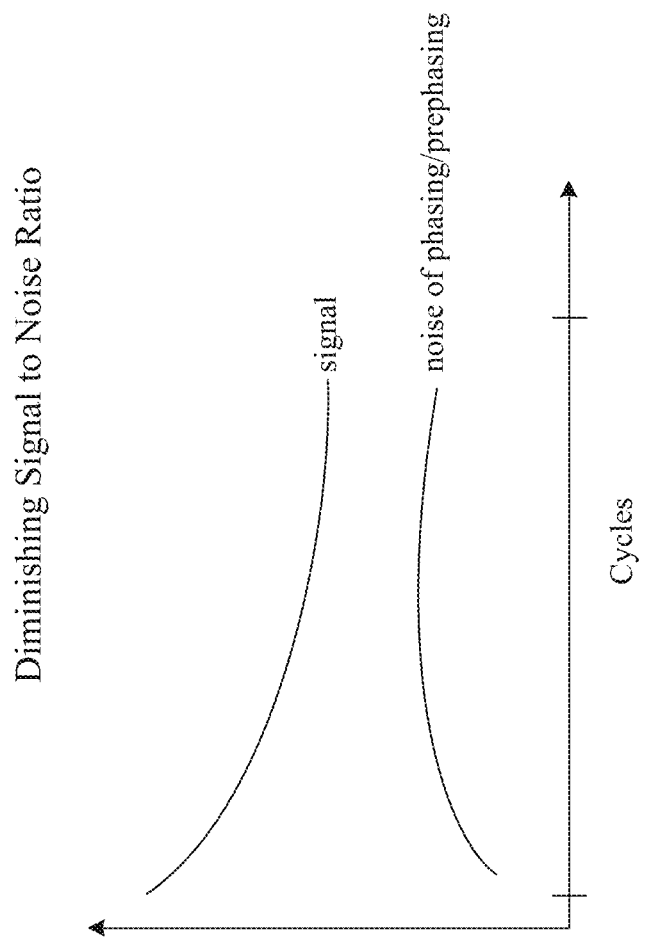
FIG. 4 conceptually illustrates a decreasing signal-to-noise ratio as cycles of sequencing progress.

FIG. 4 conceptually illustrates a decreasing signal-to-noise ratio as cycles of sequencing progress. The top curve illustrates diminishing signal. The bottom curve illustrates an increasing noise floor. The difference between signal in the noise floor decreases, taking with it the signal-to-noise ratio.

We explained above that, for the sensor studied, signal decay results from attaching tags to strands (206A) at positions that are progressively further away from the sensor (206). In addition, phasing and pre-phasing (505) reduce the signal, as they increase the noise.

Phasing and pre-phasing (505) increase noise in successive sequencing cycles, by impacting which tag fluoresces. Phasing and pre-phasing impact which sequence position is tagged and produces light in individual sample strands of an amplified cluster, with a probability distribution represented by the multinomial expansion (513). This distribution broadens as sequencing proceeds.

Decreasing the signal and increasing the noise as cycles progress, as depicted in FIG. 4, reduces the signal-to-noise ratio and complicates base calling.

Figure 5:
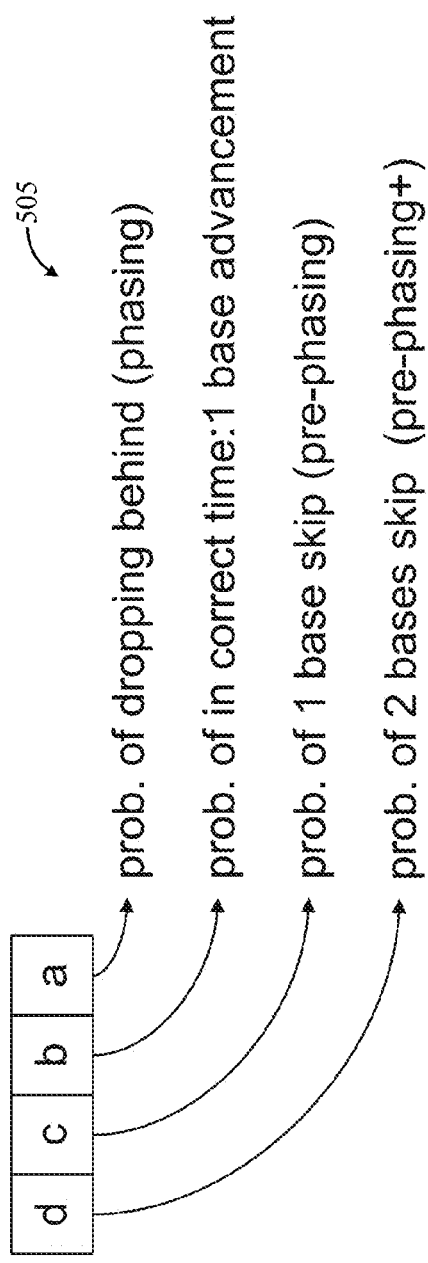
FIG. 5 illustrates use of a convolution kernel to produce an estimated matrix of signal distributions over phasing (behind), in correct time, and pre-phasing (ahead) tag fluorescence.
Figure 5:
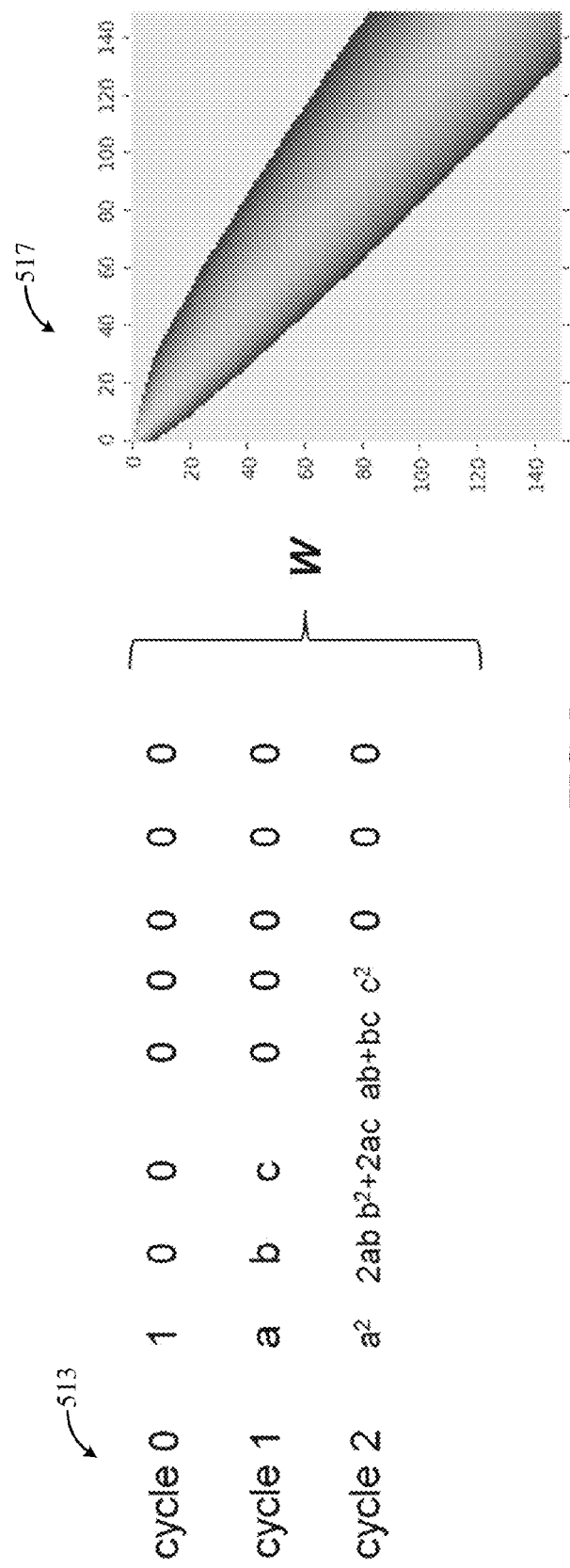
Figure 12:
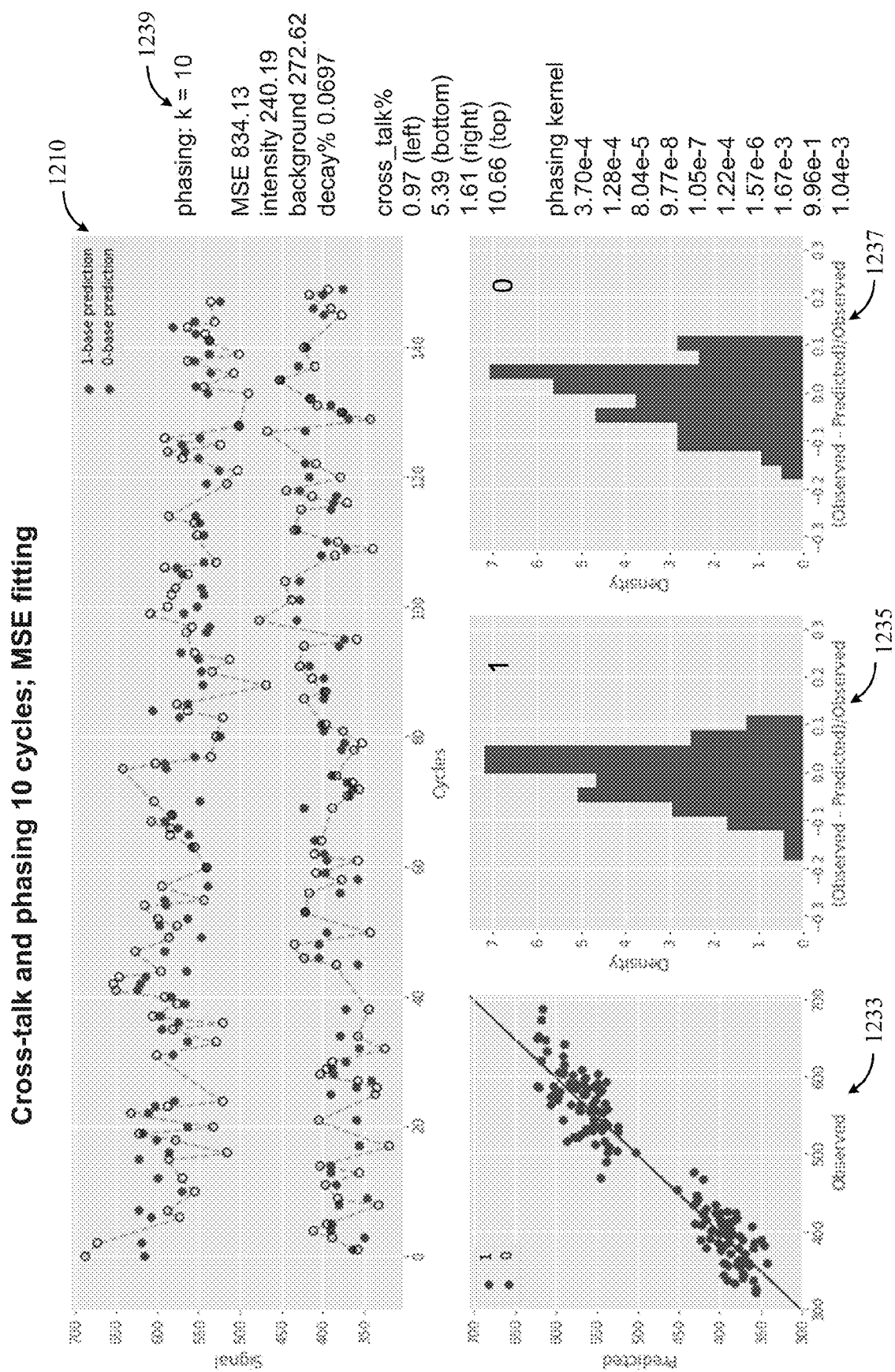

FIG. 5 illustrates use of a convolution kernel to produce an estimated matrix of signal distributions over phasing (behind), in correct time, and pre-phasing (ahead) tag fluorescence. Construction of a four-term polynomial (505) and application of a three-term polynomial (513) are illustrated. Coefficients of the polynomial add up to one or 100%, as the coefficients represent probabilities. Coefficient (a) is the probability that chemical processing during a cycle fails to advance tagging of the sequence. That is, that the nucleotide marked by a fluorescent tag stays in the same location as it was in the prior cycle. The value shown for this event, in FIG. 12, is 0.0017, or 0.17%, which is about 1/600. Coefficient (b) is the dominant probability that the process works as intended and the nucleotide marked by a fluorescent tag advances one location. This outcome has a probability of 99.7%. Coefficient (c) is the probability of pre-phasing and coefficient (d) is the probability of pre-phasing by two positions. Taken together, the probabilities of pre-phasing one or two positions, in FIG. 12, is 0.0012, or 0.12%, which is about 1/800.

The three-term polynomial is applied across cycles 0-2 (513), illustrating how the multi-nominal probability distribution of phasing and pre-phasing broadens as cycles proceed. At cycle 0, it is assumed that the initial attachment of tags is complete. This is a simplification that is useful for illustrative purposes. In cycle 1, the three-term polynomial applies dominant probability (b) that the process will operate correctly and smaller probabilities (a, c) that tagging of any individual strand will fall behind or jump ahead, respectively. In cycle 2, the three-term polynomial is multiplied by itself, producing a second order polynomial with five terms. While the second order polynomial has five terms, the probability of repeated phasing and falling behind by two cycles is only 1/36,000. The probability of repeated pre-phasing and jumping ahead by two cycles is smaller. In cycle 150, repeated multiplication of the three-term polynomial with itself produces a polynomial with 299 terms, with leading and trailing terms of $150^{th}$ order. Since only 150 intensity signals are gathered in this example, terms 151 to 299 can be ignored and not used in the estimated signal distribution matrix W.

Heat map 517 provides a visualization of how the multinomial distribution broadens as sequencing cycles progress. The distribution shape resembles a cone.

Figure 6:
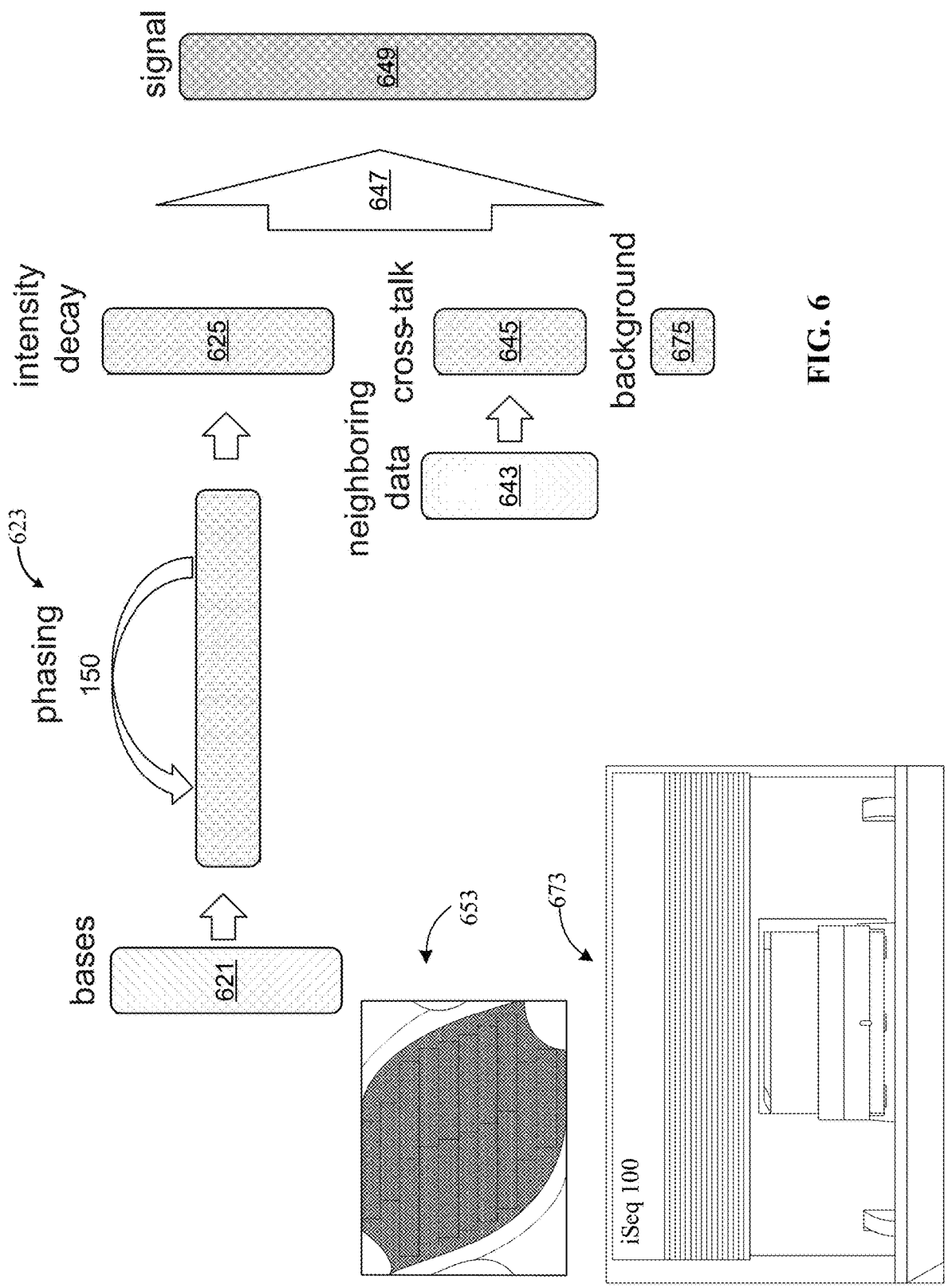
FIG. 6 is a high-level block diagram of deriving actual signals from captured intensity maps, of distinguishing signal from noise.

FIG. 6 is a high-level block diagram of deriving actual signals from captured intensity maps, of distinguishing signal from noise. A sequencing device such as the iSeq 100 (673) uses a flow cell (653), takes intensity readings, and calls bases for clusters on the flow cell. For characterization and performance analysis, the base calling can be against a previously analyzed sample. The ground truth for the sequence of the well-known sample can be in the sequencer base calling and/or prior sequencing of the sample. This ground truth is used when characterizing the sequencer's performance. With this ground truth, intensity data for a particular sensor (621) and neighboring sensors (643) can be corrected to take into account phasing (623), intensity decay (625), crosstalk (645) and background readings (675). The combination of these corrections (647) extracts the underlying signal (649) from captured intensity. In a signal present condition, the extracted signal can be less than half of the captured intensity.

Corrections for phasing (623) and for intensity decay (625) can be calculated for a particular pixel. In our example, 150 intensity the readings are available for the pixel. As sequencing proceeds, phasing and pre-phasing have an increasing impact on whether intensity readings measured are for the current position/cycle or for positions before or after the ideal position for the current cycle. Since intensity readings are available for the entire read, for 150 positions/cycles in this example, data from both prior and subsequent positions can be used to make the phasing correction (623). This correction can be made using a position-dependent 1D convolution. The position-dependent convolutions for the 150 positions can be held in the 150×150 signal distribution estimate matrix W. Similarly, intensity decay (625) can be corrected for the particular pixel, on a position-dependent basis. Factors for intensity decay correction can be held in the 150×1 estimated decay vector d.

Correction for crosstalk (645) depends on intensity readings of neighboring pixels (643). A portion of values from the neighboring intensity readings increases the intensity reading of the particular pixel. Crosstalk coefficients are pixel dependent. While crosstalk is cycle dependent, the dependency relates to intensity in neighboring pixels; the crosstalk coefficients can be calculated once, without dependence on the cycle.

A background intensity level also contributes to the intensity reading for particular pixel. As a first approximation, a general background level can be used. Performance is likely to improve when a particular background level is used for a particular pixel, as will be explained below, in the context of FIGS. 14A-B and 15.

Coefficients for performing these corrections, for instance using the formula above, can be fit by using mean square error as a loss function during gradient descent training. Ground truth for whether a signal is present in a particular intensity channel is available from the base calling of the sample. Coding this truth as a Boolean value multiplicatively injects (1) or removes (0) the signal term for the particular pixel.

Relatively few parameters need to be fit in order to formulate these corrections. In the particular pixel term, the estimated decay vector needs to be fit. After fitting, the only unknown is the underlying signal, which is derived from the other values. In the crosstalk term, for crosstalk coefficients need to be fit taken to account contributions from four neighboring pixels. Alternatively, more coefficients could be used to take into account more neighboring pixels. For instance, if hexagonal pixels were used in the square pixels, crosstalk would come from six neighbors. Or for a patch. Or for a checkerboard patch of nine pixels, all the neighbors could be used. In the background term, a single coefficient can be fit or a coefficient can be fit for each particular pixel. Fitting coefficients for each particular pixel can be based on the individual pixel work and take into account crosstalk from neighboring pixels that may have different background levels. A method is described below for calculating pixel-specific background coefficients that take into account crosstalk from the neighboring pixels. With so few coefficients to fit, gradient descent can calculate the coefficients efficiently. In practice, training benefited from varying the learning rate. Dropout was not required to avoid over fitting.

Relative Contribution of Corrections

Each of the corrections analyzed is valuable by itself. Discussion of their relative value and combined value follows. Residual errors after correction were evaluated and heat maps were generated to confirm the spatial distributions of contributions to intensity the readings. FIGS. 7-12 depict predictions and intensity readings for a sequence of 150 cycles, when various corrections were applied. FIG. 13 illustrates heat maps generated to visualize spatial distribution of contributions by various factors to the measured intensity at individual pixels.

Figure 7:
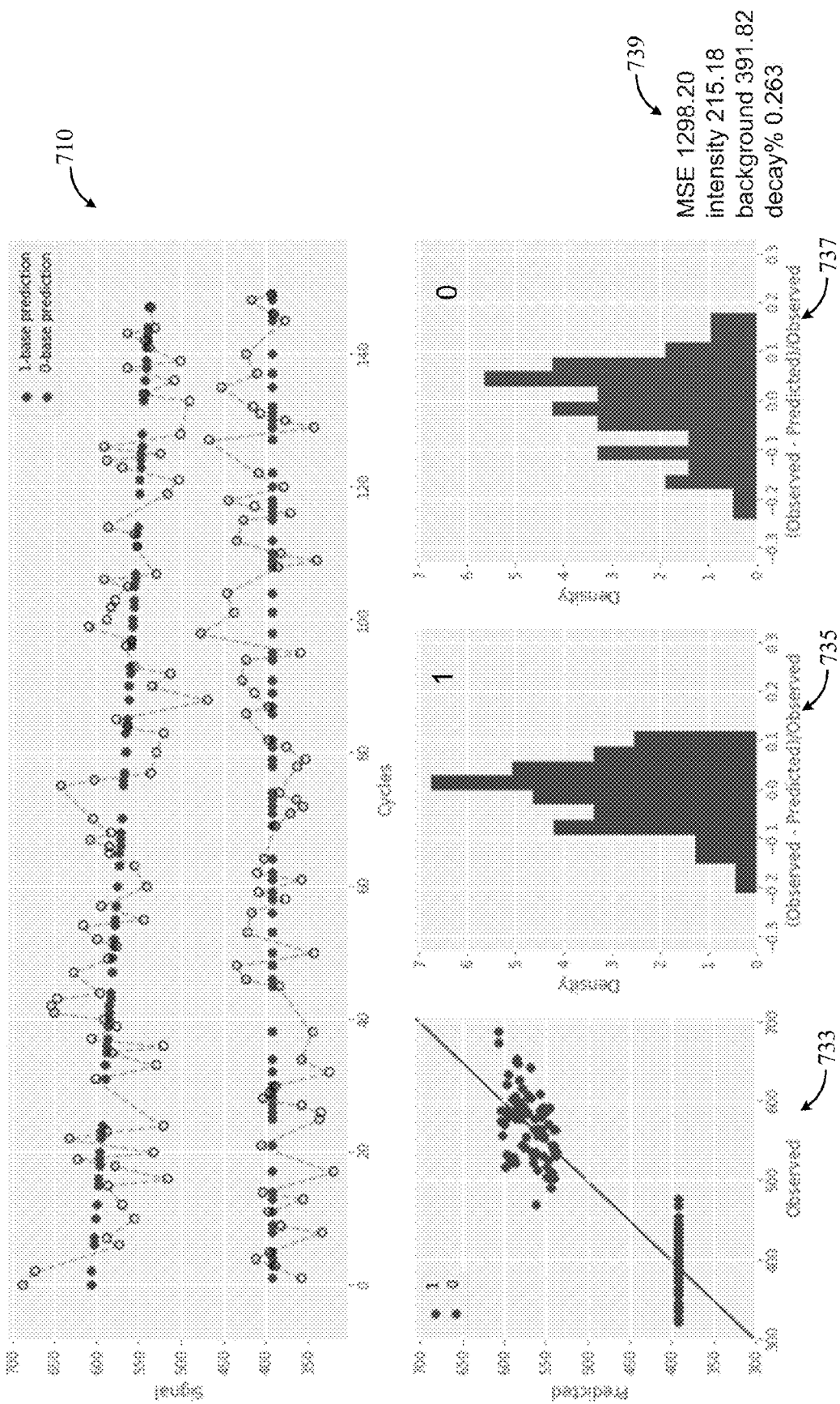
FIG. 7 illustrates analysis of 150 cycles in one run with corrections for just the decay and background.

FIG. 7 illustrates analysis of 150 cycles in one run with corrections for just the decay and background. Note that just one run is shown, one particular pixel. After fitting, the residual mean square error was 1298.20. Predictions represented as solid dots and actual data represented as hollow dots are depicted in the upper panel (710). Predictions are applied to a particular intensity channel for no signal and signal present conditions, ignoring crosstalk and phasing. In lower wine, for the no signal condition, predicted solid dots are at the background level 391.82 (739). Actually readings are scattered above and below the prediction. Residual errors are the difference between predicted and actual values. Gaps in the lower line of solid dots complement solid dots in the upper line. In the upper line, predicting the signal present condition, the solid dots slope downward from 391.82+215.18=607, to approximately 540 at cycle 150 as decay impacts the signal.

Panel 733 is a scatter plot of predicted versus actual or observed values for the clusters of no signal and signal present cycles. Panels 735 and 737 are normalized histograms of residual error between predicted and observed values. panel 735 is for the signal present condition and panel 737 for the no signal condition. Values derived from this characterization (739) include a mean squared error of 1298.20, a background intensity of 391.82, a signal intensity of 215.18 and a per cycle decay of 0.263%.

Figure 8:
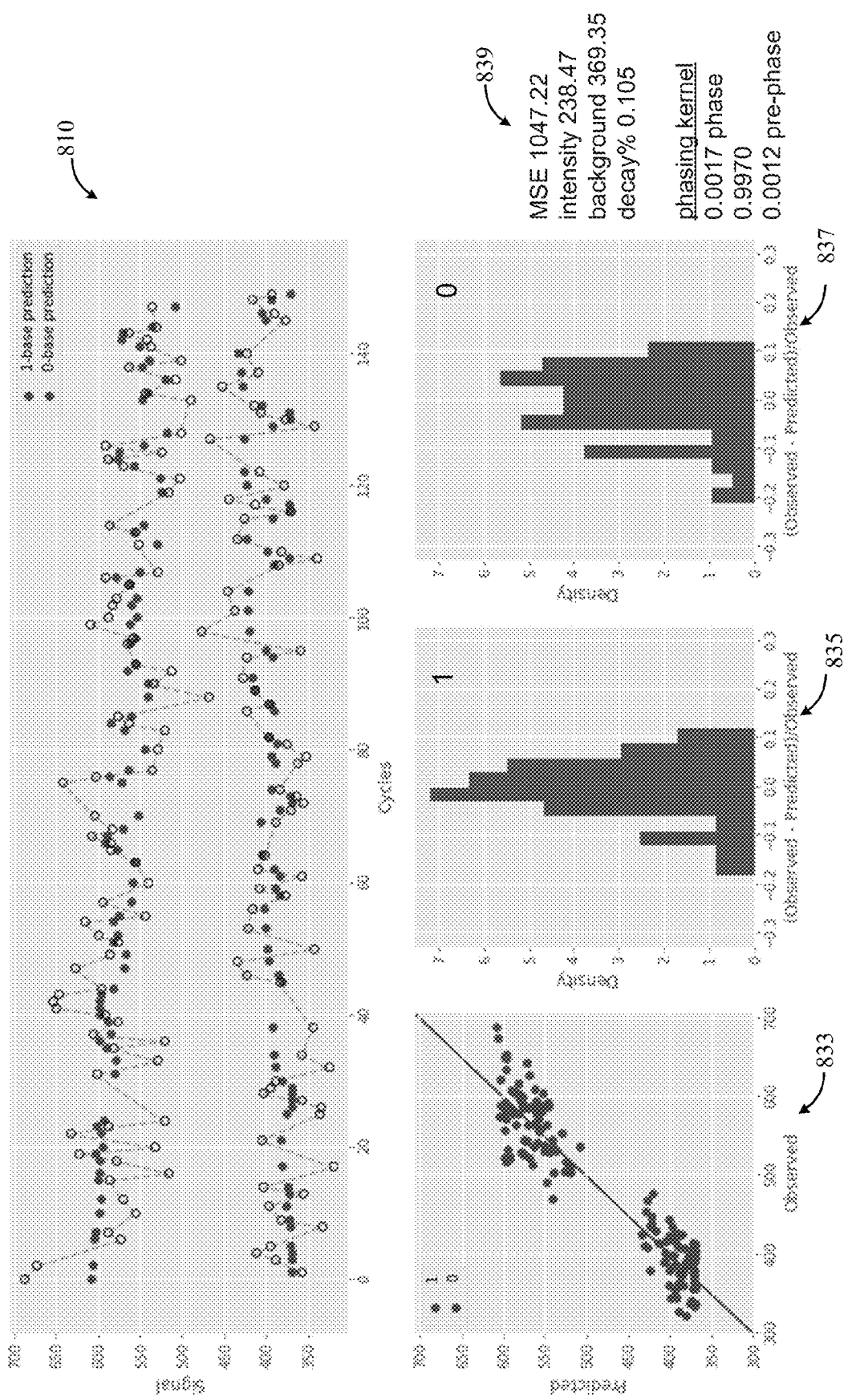
FIG. 8 illustrates analysis of 150 cycles and one run with correction for phasing, in addition to decay and background.

FIG. 8 illustrates analysis of 150 cycles and one run with correction for phasing, in addition to decay and background. Phasing distribution is represented by a three-term polynomial with a single cycle phasing probability of 0.17%, a correct behavior probability of 99.70%, and the pre-phasing probability of 0.12%. After fitting, the residual means where error was reduced to 1047.22. In the top panel 810, predictions and actual values are depicted in solid and hollow dots. The predicted lines are no longer straight. Improvement of the predicted values in following variation of the actual values is sometimes visible. For instance, the predicted no signal condition before and after cycle 100 goes up and down with actual observations. The signal present condition around cycle 80 also has predictions that more closely track observations.

Panel 833 shows a distribution cloud, instead of a constant predicted value of the no signal condition. The distributions in panels 835 and 837 are somewhat tighter than they were without taking into account phasing. Values derived from this characterization (839) include a mean squared error of 1047.22, a reduced background intensity of 369.35, an increased signal intensity of 238.47, with the decreased per cycle decay of 0.105%.

Figure 9:
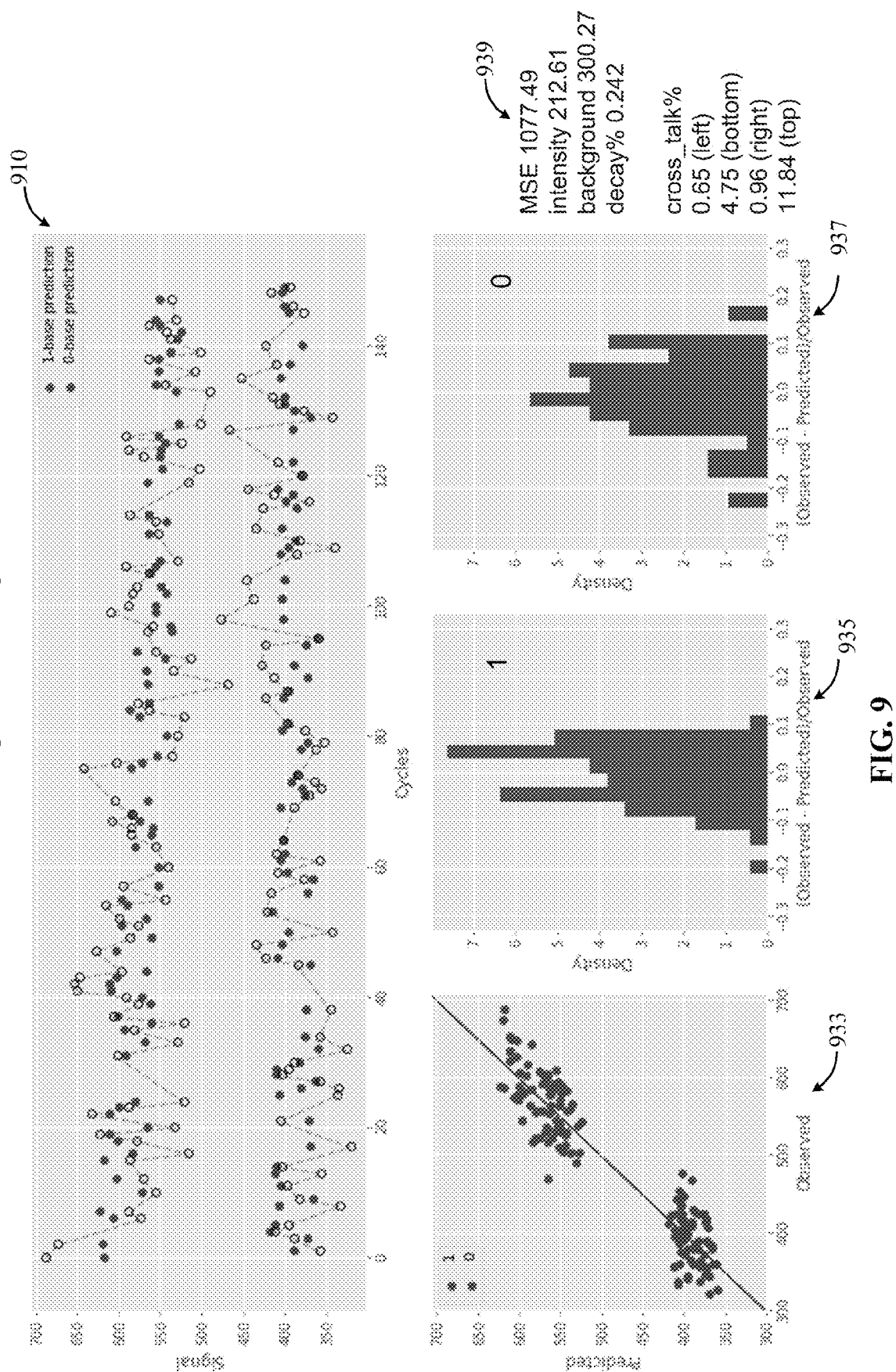
FIG. 9 illustrates analysis of 150 cycles in one run with correction for crosstalk, instead of phasing.

FIG. 9 illustrates analysis of 150 cycles in one run with correction for crosstalk, instead of phasing. Correction for crosstalk did not reduce residual square error as much as correction for phasing. Mean squared residual error was 1077.49. The top panel 810 illustrates that taking into account crosstalk decreased the calculated background to 300.27 with a significant contribution to intensity coming from neighboring pixels.

Panel 933 shows clouds that are rotating to become more aligned to the solid diagonal line. The distributions in panels 935 and 937 have outliers that are not well predicted by correcting for crosstalk. Values derived for this correction (939) include a mean squared error of 1077.49, a reduced background intensity of 300.27, the signal intensity of 212.61 and a per cycle decay of 0.242%. The calculated crosstalk is substantially higher from the top neighboring pixel then from the writer left. Crosstalk coefficients, after fitting, were 11.84% from the top, 4.75% from the bottom, 0.65% from the left and 0.96% from the right.

Figure 10:
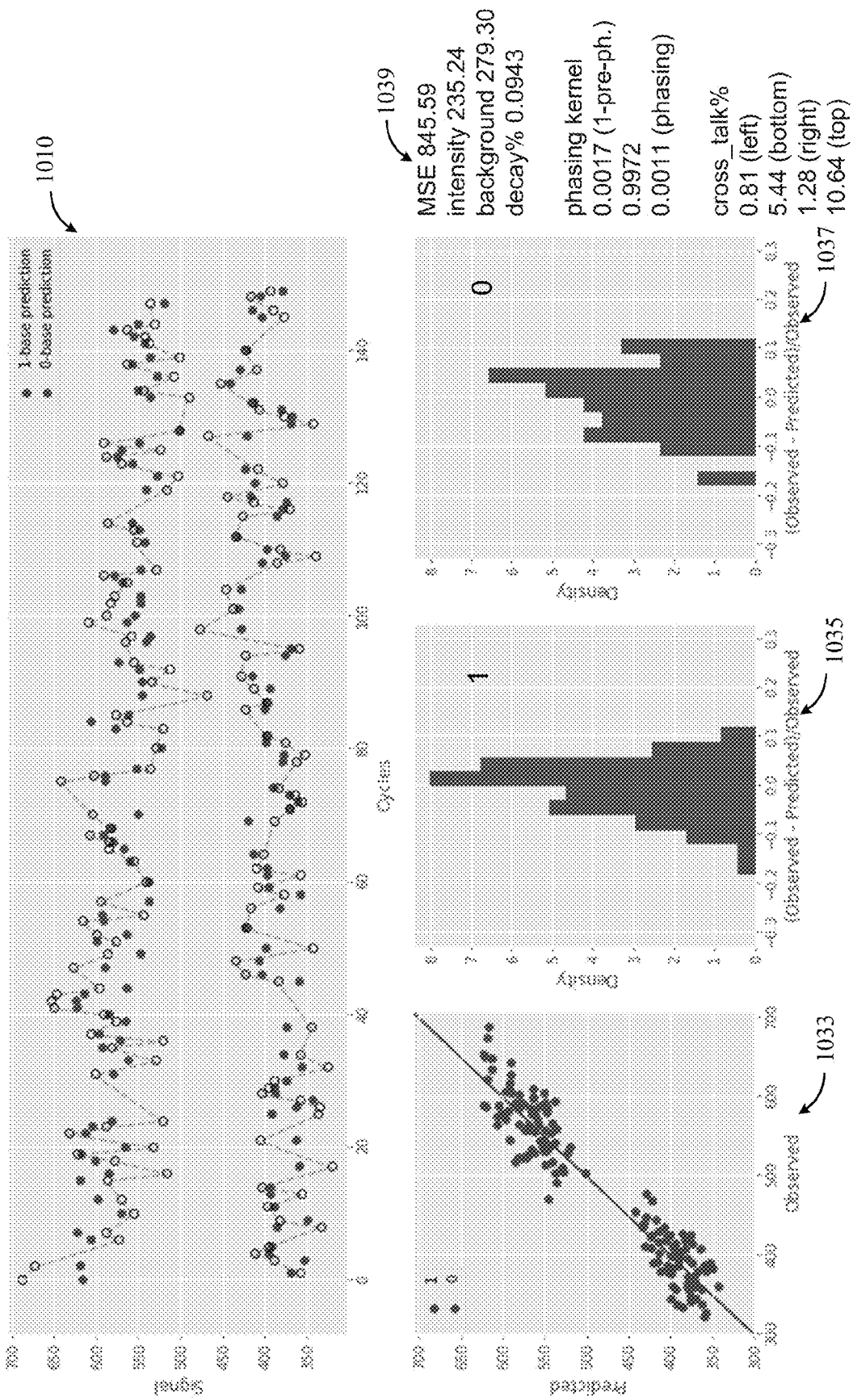
FIG. 10 illustrates combining correction for phasing in crosstalk in addition to estimation of background, intensity and decay.

FIG. 10 illustrates combining correction for phasing in crosstalk in addition to estimation of background, intensity and decay. Correction for both phasing and crosstalk significantly reduced the residual mean square error to 845.59, applying the same three-term polynomial phasing kernel as in FIG. 8. In the top panel 810, predictions go up and down with actual observations especially after cycle 40 with very little overshoot in the predictions.

Panel 1033 shows clouds that are nicely scattered around the solid diagonal line. Residual error history in panels 1035 and 1037 are increasingly tight distributions with some SKU in the no signal prediction due to an outlier. The outliers of lower predicted then observed values can be seen just after cycle 20, just before cycle 100 and just before cycle 130. Values drive for this correction (1039) include a mean squared error of 845.59, a lower background of 279.30, the signal intensity of 235.24 and a reduced decay per cycle of 0.0943%. The crosstalk coefficients show a decrease in crosstalk from the top and slight increases from other neighboring pixels. Crosstalk coefficients were 10.64% from the top, 5.44% from the bottom, 0.81% from the left and 1.28% from the right.

Figure 11:
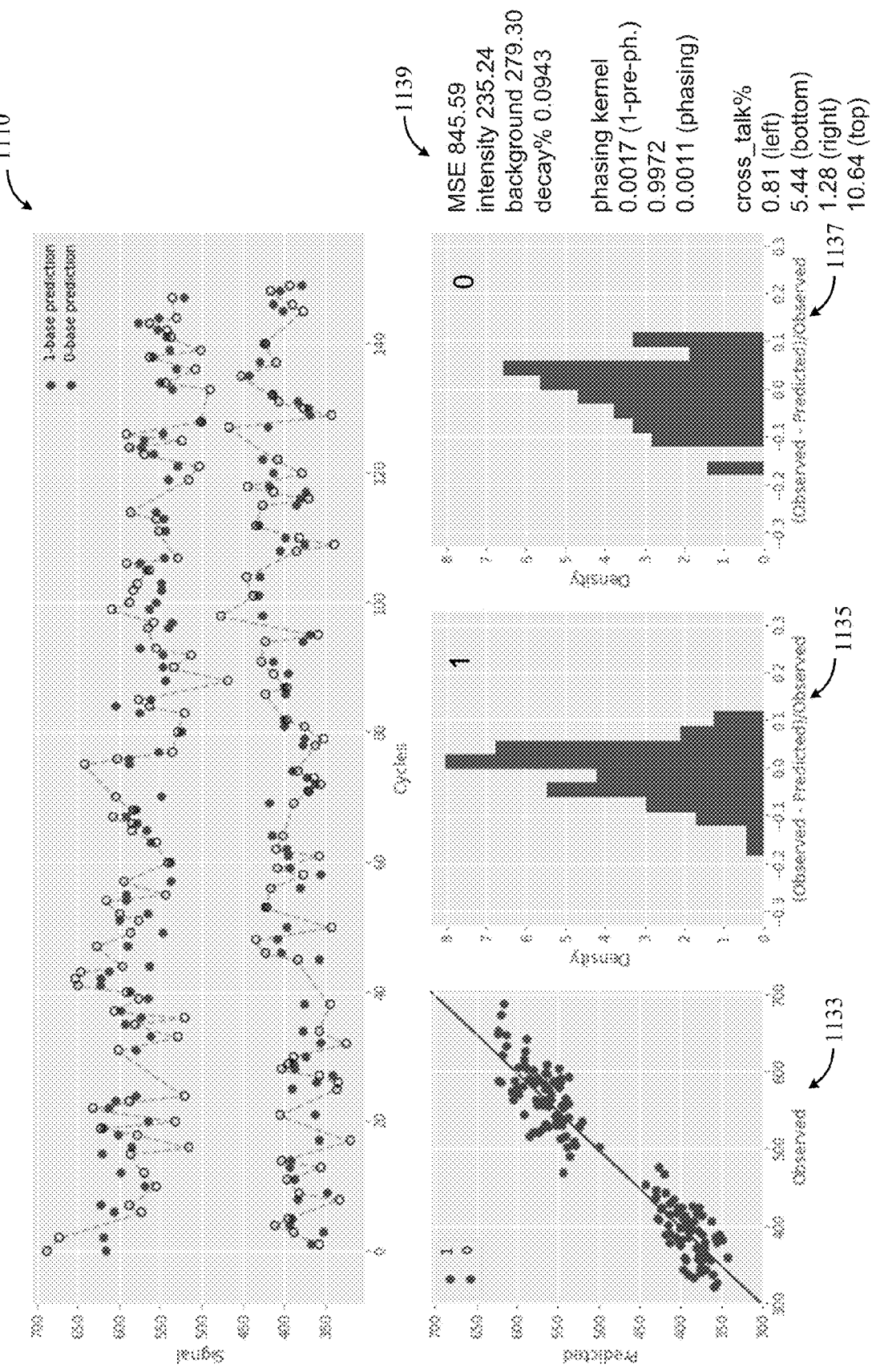
FIGS. 11 and 12 analyze using expanded phasing kernels, expanded to five-and ten-term polynomials that handle up to 3 and 8 pre-phasing skips, respectively.

FIGS. 11 and 12 analyze using expanded phasing kernels, expanded to five-and ten-term polynomials. FIG. 11 illustrates expanding the phasing kernel from 3 to 5 cycles, covering pre-phasing by up to three skips. Expansion of the phasing kernel increases the number of pre-phasing forward skips accounted for in a particular cycle; in contrast, phasing can only result in falling behind by one position per cycle, so the number of phasing coefficients remains one. Increased correction for pre-phasing from one to three skips only reduced the mean squared error from 845.59 to 844.04, which produces very little change in any of the visualization panels between FIGS. 10 and 11. Small improvements in background, intensity and per cycle decay resulted. Calculated crosstalk from top and right pixels increased marginally while crosstalk from bottom and left pixels was unchanged.

FIG. 12 illustrates expanding the phasing kernel further to 10 cycles, covering up to eight skips. The probability of correct tagging performance is slightly reduced in this kernel from 99.70% to 99.6%. This extreme correction for pre-phasing only reduced the mean squared error to 834.13. Background slightly decreased, intensity slightly increased and decay slightly decreased. The most apparent feature among the visualization panels is in 1237, where two-thirds of the low outlier points from panel 1137 are brought closer to the center of the distribution.

Figure 13B:
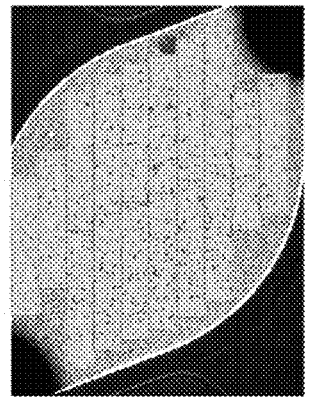
Figure 13A:
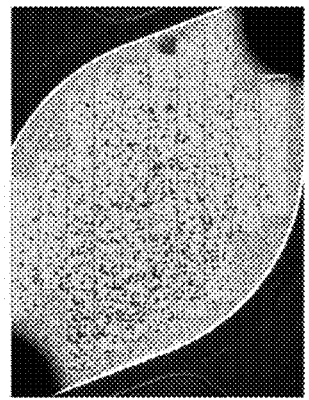
Figure 13F:
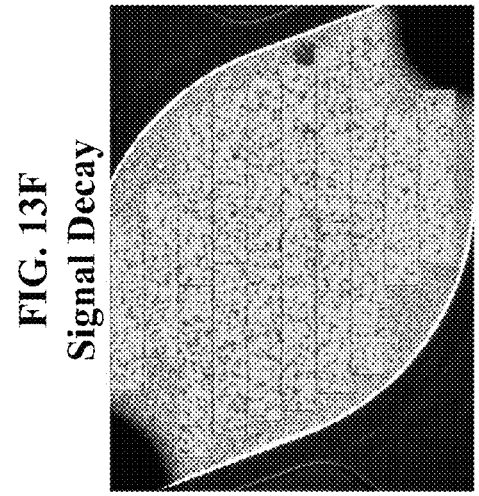
Figure 13E:
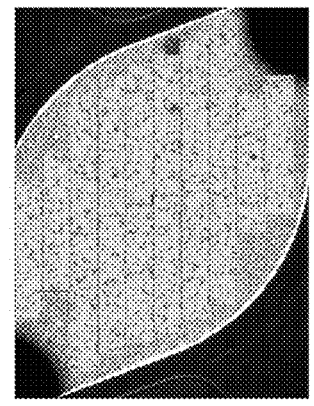
Figure 13D:
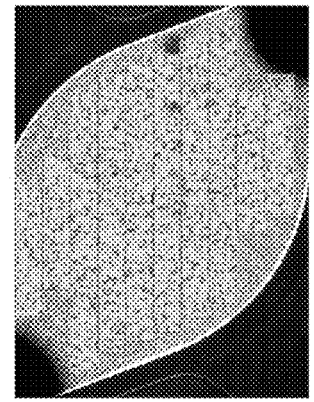

FIGS. 13A-F are a series of heat maps created by applying false color to a photograph of a flow cell, based on analysis of contributions of various factors to measured intensities in an intensity map for one channel. The factors analyzed and visualized are contributions of background illumination (FIG. 13A), background sensor variation (FIG. 13B), cross talk from neighboring pixels (FIG. 13C), phasing and pre-phasing (FIGS. 13D-E), and signal decay (FIG. 13F). Over 150 cycles, parameters were separately calculated for each pixel.

The phasing, pre-phasing and signal decay maps indicate uniform distributions of variation. For instance, the visualization of signal decay (FIG. 13F) does not show any apparent pattern, except at the exit from the flow cell in the bottom right corner. This exit area shows variation in all of the heat maps. Heat maps for phasing and pre-phasing (FIGS. 13D-E) also have uniform distributions, excepting a red colorized splotch just to the left of the dark, uncolorized splotch, five rows from the bottom. A difference in color between the phasing and pre-phasing in the heat maps indicates that phasing is slightly more likely than pre-phasing. The uniform distributions in heat maps indicate random variations of several factors during sequencing, as expected.

FIG. 13A-B separate background illumination effects from sensor-specific background reading biases. The background illumination heat map (FIG. 13A) indicates brighter illumination on the left side of the flow cell than on the right side. Apart from illumination effects, the sensor-specific biases on background readings is mapped in FIG. 13B. This apparent manufacturing or design artifact was larger than expected, as discussed below in the context of FIGS. 14A-B.

FIG. 13C maps relative crosstalk contributions of top, bottom, left and right adjoining pixels. The largest contributor by far is the top pixel, located north of the center pixel that is generating a signal. The bottom pixel contributes more crosstalk than either left or right neighboring pixels. (However, analysis below suggests that this estimation may be biased.)

For manufacturing and design, these heat maps characterize performance of this particular flow cell in a way that suggests design and manufacturing improvements. Illumination is not quite uniform, could be improved. Systematically greater crosstalk from the top and bottom pixels suggests potential design or manufacturing improvement, or could simply be a consequence of asymmetry in placement of dominant and secondary wells in a dual well design (300B). The red colorized splotch just to the left of the dark, uncolorized splotch, five rows from the bottom, suggests a manufacturing defect to be investigated by deconstruction of this particular flow cell. The red colorized splotch at the outlet of the flow cell, in the bottom right corner, may indicate an opportunity for design improvement. Thus, characterization of flow cell performance leads to manufacturing and design improvements.

For inference and base calling during production, these heat maps confirm the coefficients derived and general applicability of the corrections identified. Accurate identification of factors to be corrected leads to informed design of inputs to and structure of a deep learning system.

FIGS. 14A-B reflect sensor-specific variation in background readings that is not randomly distributed. The 2d histogram in FIG. 14A revealed that there are background reading levels for the no signal condition in three ranges, around 250, 750 and 900, as indicated by arrows. The std histogram in FIG. 14B confirmed three distinct background levels, in steps to the left of the vertical dashed line. As an improvement to the model, individual pixel background levels were set, instead of having a uniform sensor background reading.

FIG. 15 presents a background level hyper-parameter approach to setting a particular pixel's background level taking into account background levels of its neighbors. A subject of analysis in FIG. 15 is whether to adjust a pixel level by its minimum background level in the no signal condition or by slightly less than the minimum background level. One approach to shifting the signal level of a particular pixel would be to subtract the minimum signal level for that pixel (in that intensity channel) over the cycles measured. A minimum signal level corresponds to the no signal condition, as opposed to the signal present condition. It is intuitively appealing to subtract the full minimum value, but analysis showed that subtracting somewhat less produced better corrections. Graph 1513 shows measured intensity values for both no signal and signal present conditions for a particular pixel, in red, and values of four neighboring pixels, in blue. The particular pixel was selected because neighboring pixels included clusters. For each of the five pixels, there are distinct lines for no signal and signal present conditions. However, these distinct lines are relatively close together in graph 1531 and not visually distinguishable for the neighboring pixels.

Graph 1515 depicts the effect on mean squared error of adjusting intensity values by 90 to 100% of the minimum intensity value for the particular pixel. As expected, adjusting individual pixels by subtracting increasing portions of their minimum background level improves the mean squared error. Surprisingly, the improvement stops at 99% of the minimum intensity value and turns back upward when 100% of the minimum intensity value is used as an adjustment factor. This observation can be tested by creating a free parameter, shrinkage_limit:

Shifted_signals=signals−(min(signals)*
shrinkage_limit), where signals is a vector of measured intensities of a pixel in a channel, min(signals) is the minimum value in the vector, and shrinkage_limit is a hyper parameter typically in a range of 0.90 to 1.00.

In this example, analysis of mean square errors for small variations in the shrinkage_limit hyper parameter revealed a best correction at 0.99.

Graph 1517 shows distributions of pixel intensity readings, reduced by 0.99* min(signals) for the five pixels, plotted on a rescaled graph. Instead of a plot over the intensity level range from 0 to 1000, this graph, after adjustment, plots intensity levels over a range from 0 to 225. Upper sequences of dots, for the signal present condition, are visually separated from lower sequences of dots, for the no signal condition. In tables 1521 and 1527, estimated mean squared error reportedly was substantially reduced and bias removed from crosstalk estimations. The mean squared error was reduced from 82.85 to 57.54. The big reduction in mean squared error resulted from pixel-by-pixel adjustment to remove a large portion of background from the intensity readings.

At this pixel location, tables 1521 and 1527 indicate that crosstalk from the top pixel was not dominant. Removal of bias produced an estimate that crosstalk from neighbors was nearly equal. This is less suggestive of a manufacturing or illumination angle issue than appeared from the crosstalk coefficients of FIGS. 7-13. In tables 1523 and 1529, parameters for the center or red pixel, before and after adjustment, are given.

While the intensity signal dropped somewhat, it is no longer a small proportion of the background level. The decay estimation increased slightly. The phasing and pre-phasing estimations decreased slightly.

FIG. 16 includes tables that illustrate reduced estimates of crosstalk after accounting for multiple background levels intrinsic to individual sensors. The tables include data for median values of crosstalk coefficients among pixels whose neighbors include DNA clusters. Two intensity channels, for red and green laser illumination, are indicated for three different flow cells. Crosstalk coefficients for top, bottom, left and right neighbors are given. After adjustment, estimated crosstalk coefficients were half or less of the originally estimated coefficients. For the pixels analyzed, adjustment based on intrinsic background levels of sensors eliminated the appearance that crosstalk from the top neighbor dominated crosstalk from other neighbors, which appeared in FIGS. 7-13.

Figure 18:
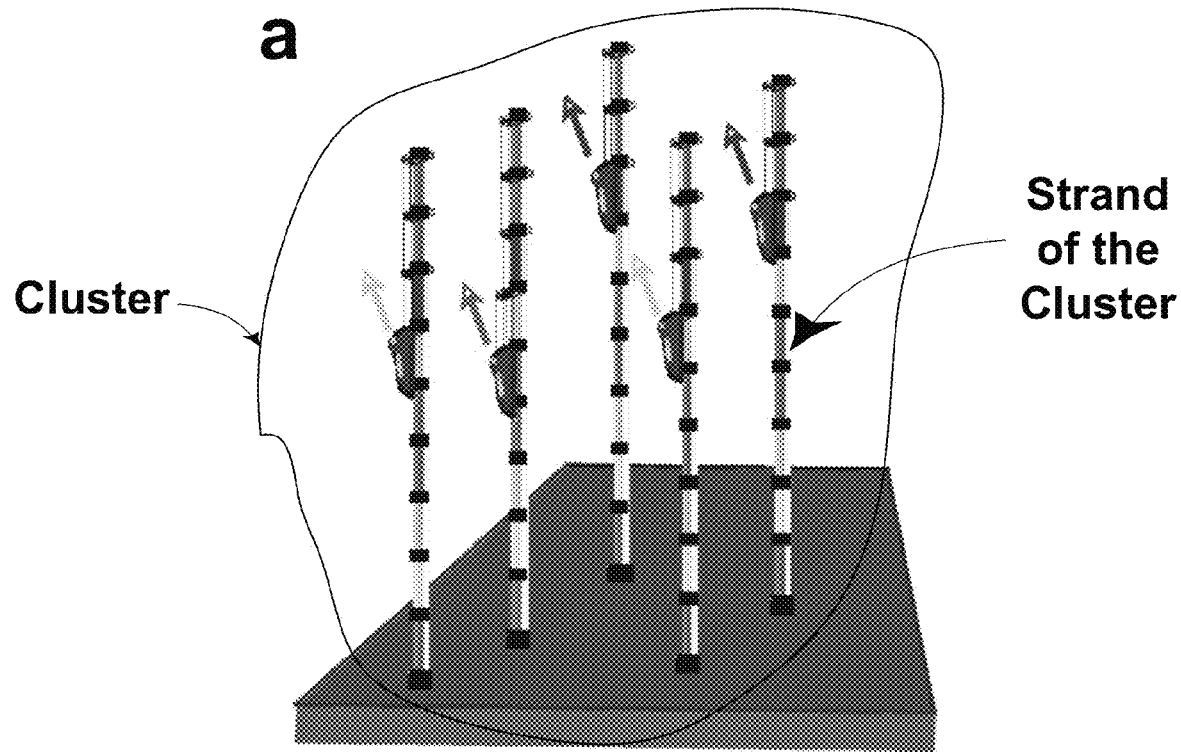
FIG. 18 illustrates one example of the phasing and pre-phasing effect.
Figure 18:
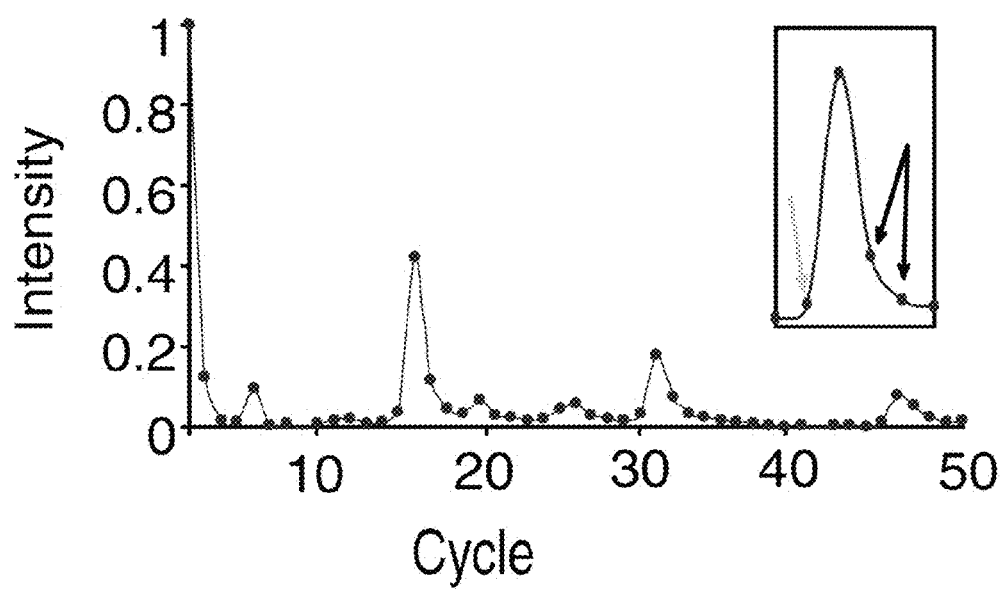

FIG. 18 illustrates one example of the phasing and pre-phasing effect.

Figure 19:
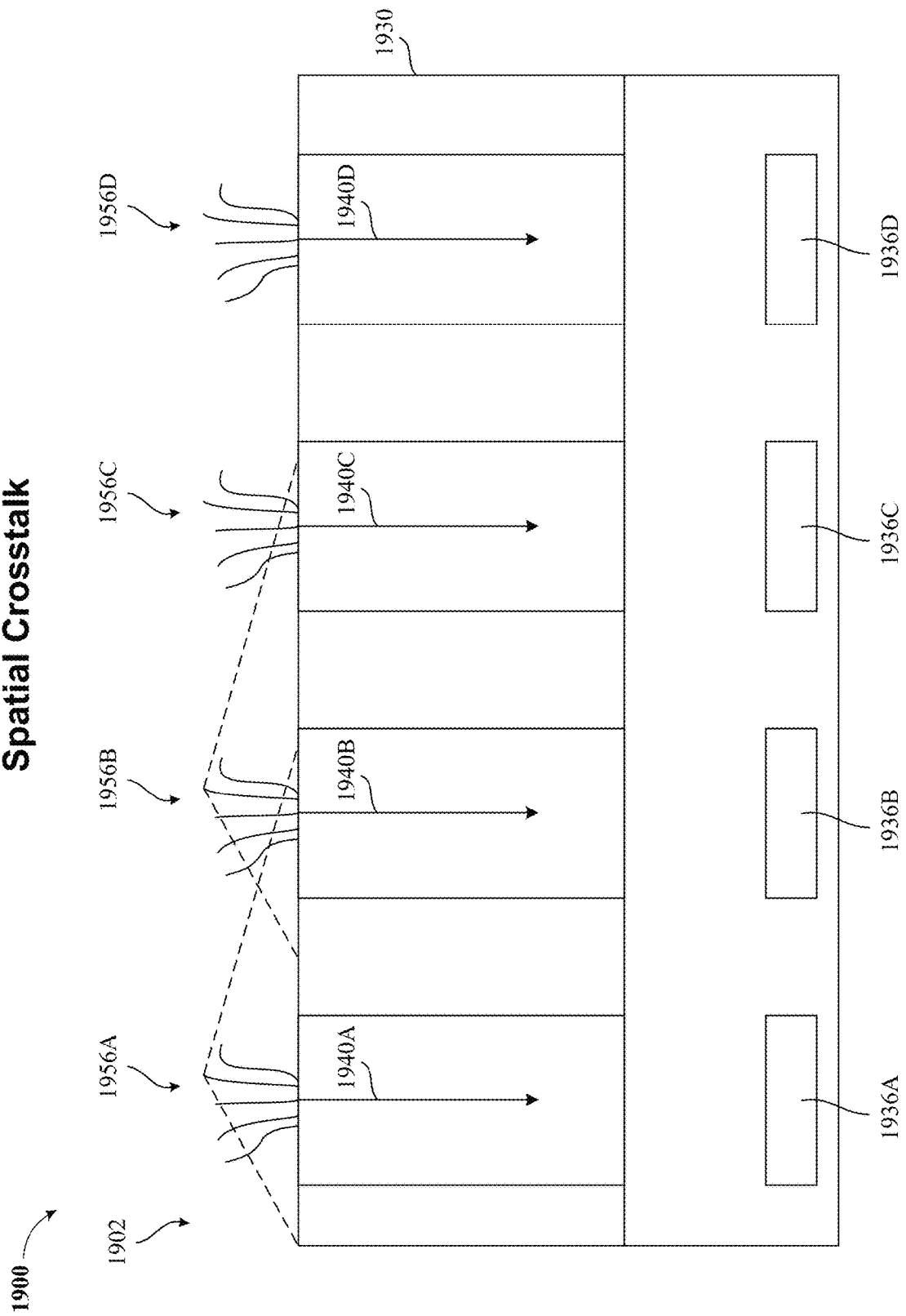
FIG. 19 illustrates one example of spatial crosstalk.

FIG. 19 illustrates one example of spatial crosstalk.

Figure 20:
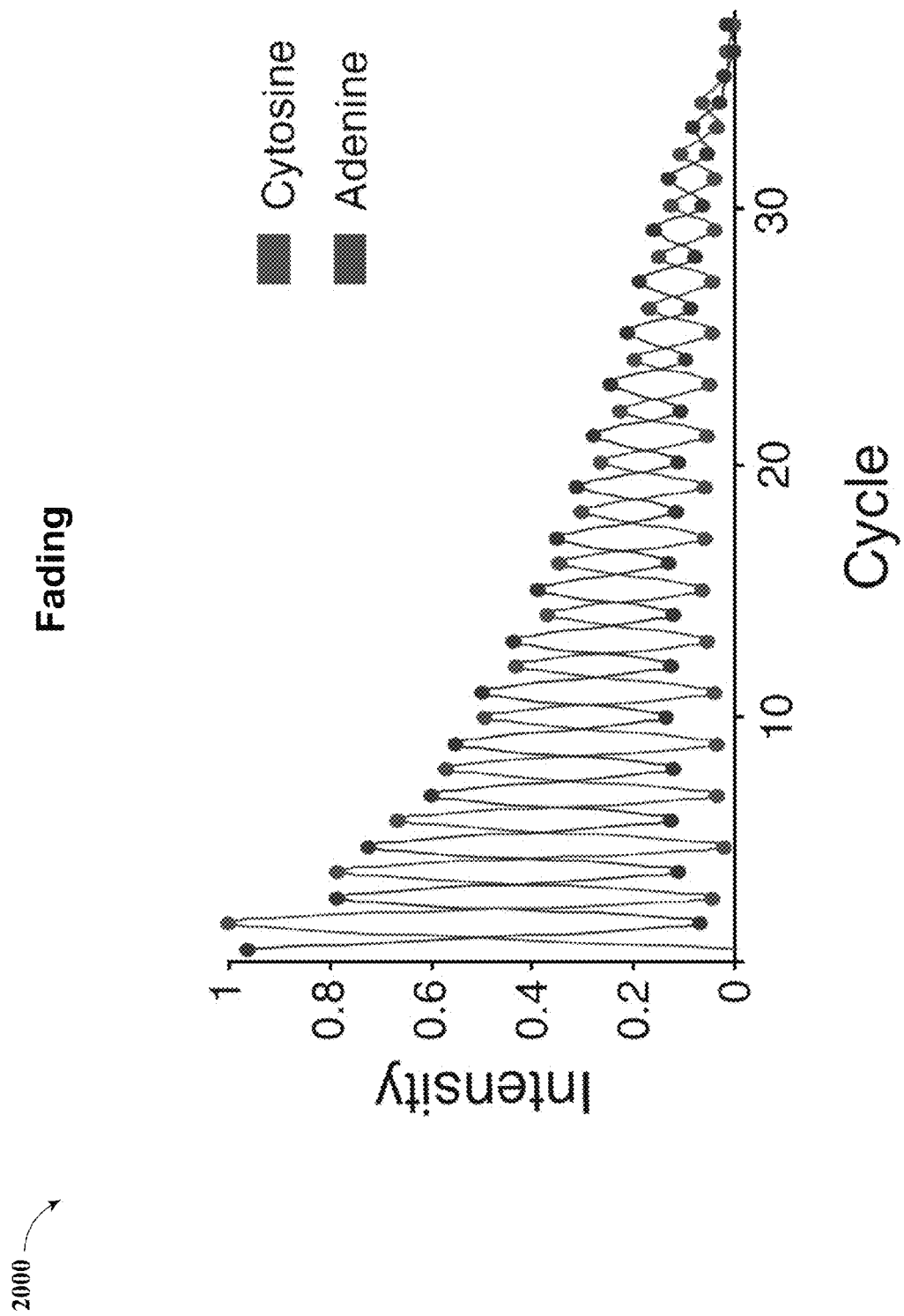
FIG. 20 illustrates one example of fading.

FIG. 20 illustrates one example of emission overlap.

Figure 21:
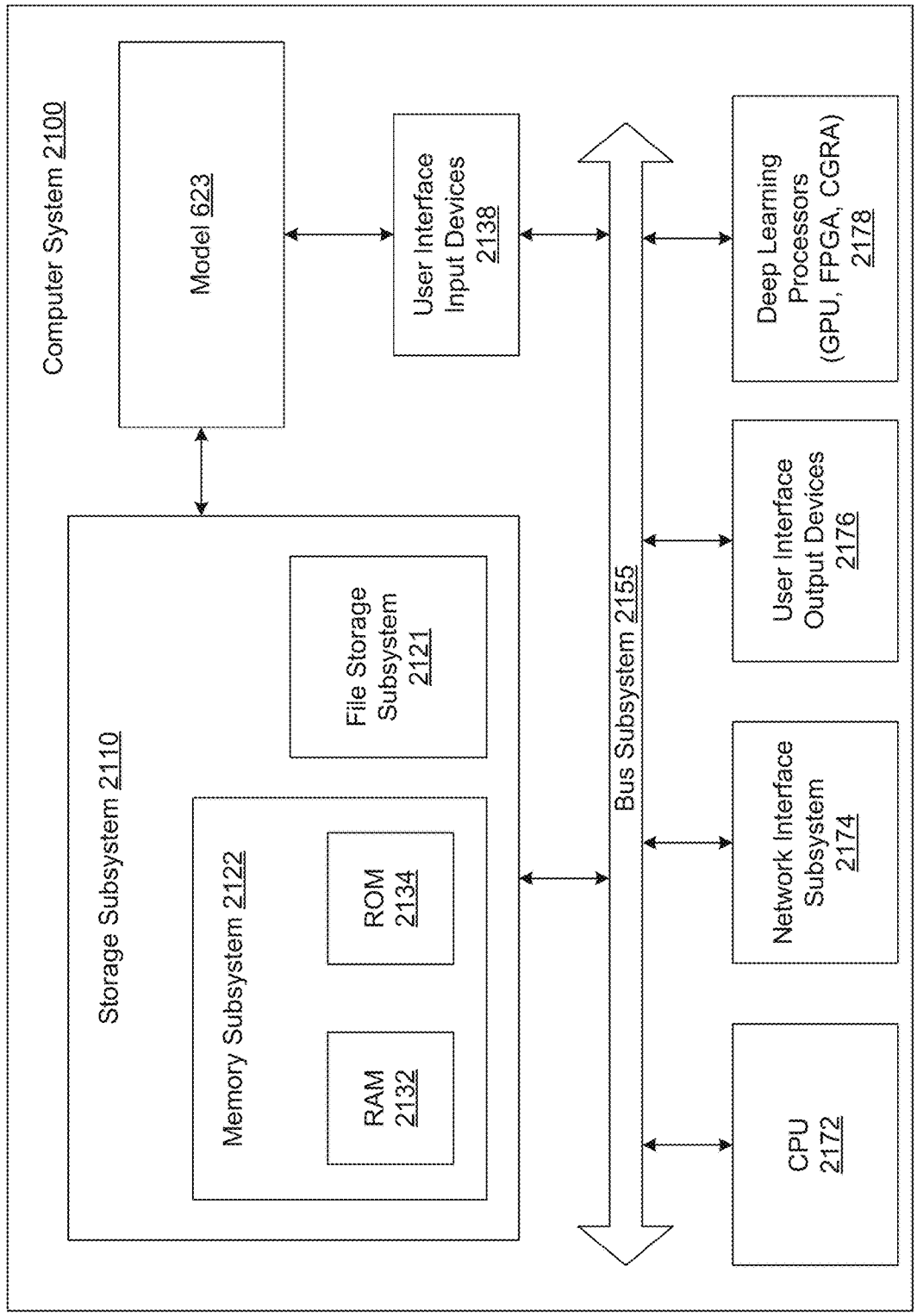
FIG. 21 is a computer system that can be used to implement the technology disclosed.

FIG. 21 illustrates one example of fading.

FIG. 22 is a computer system that can be used to implement the technology disclosed.

In the ideal situation, the lengths of all nascent strands within an analyte would be the same. Imperfections in the cyclic reversible termination (CRT) chemistry create stochastic failures that result in nascent strand length heterogeneity, introducing lagging (too short) and leading (too long) nascent strands within the analyte and reduces the purity of signal output from the interrogated position by contamination with signals from adjacent nucleotides. Phasing and prephasing effect refers to contamination of the signal for a specific cycle by the signal of the cycles before and after. Phasing and pre-phasing leads to the loss of synchrony in the readout of the sequence copies of an analyte.

Phasing is caused by incomplete removal of the 3' terminators and fluorophores as well as sequences in the analyte missing an incorporation cycle. Prephasing is caused by the incorporation of nucleotides without effective 3'-blocking. Phasing and prephasing effect is a nonstationary distortion and thus the proportion of sequences in each analyte that are affected by phasing and prephasing increases with cycle number; hampering correct base identification and limiting the length of useful sequence reads.

Incomplete extension due to phasing results in lagging strands (e.g., t−1 from the current cycle). Addition of multiple nucleotides or probes in a population of identical strands due to prephasing results in leading strands (e.g., t+1 from the current cycle). Other terms used to refer to phasing and phasing include falling behind, moved ahead, lagging, leading, dephasing, post-phasing, out-of-phase, out-of-sync, out-of-step nucleotide synthesis, asynchronicity, carry-forward (CF), incomplete or premature extension (IE), and droop (DR).

FIG. 18 illustrates one example of the phasing and prephasing effect 1800. FIG. 18a shows that some strands of an analyte lead (red) while others lag behind (blue), leading to a mixed signal readout of the analyte. FIG. 18b depicts the intensity output of analyte fragments with "C" impulses every 15 cycles in a heterogeneous background. Notice the anticipatory signals (gray arrow) and memory signals (black arrows) due to the phasing and prephasing effect 1800.

Spatial crosstalk refers to a signal or light emission from one or more non-associated analytes (or pixel areas) that is detected by a corresponding light detector of an associated analyte (or pixel area). Spatial crosstalk is caused by unwanted emissions from adjacent analytes. Ideally, the intensities of each analyte should correspond to just one analyte sequence. However, the observed intensities often contain signals from neighboring analyte sequences, other than the interrogated/target one, and, hence, are not pure.

FIG. 19 illustrates one example of spatial crosstalk. FIG. 19 illustrates a detection device 1900 having a plurality of pixel areas 1956A-1956D on a detector surface 602. The detection device 1900 includes light sensors 1919A-1919D. The light sensors 1919A-1919D are associated with and correspond to the pixel areas 1956A-1956D, respectively. Corresponding detection paths 1940A-1940D extend between the light sensors 1919A-1919D and corresponding pixel areas 1956A-1956D. The arrows that indicate the detection paths 1940A-1940D are merely to illustrate a general direction that the light propagates through the respective detection path.

During an imaging event, the detection device 1900 is configured to detect light using the light sensors 1919A-1919D. As demonstrated in FIG. 19 by pyramidal hash marked areas or zones, light emissions (or emission signals) are propagating from the pixel areas 1956A and 1956B, but light emissions are not propagating from 1956C or 1956D. The light emissions may be indicative of, for example, a positive binding event between the analytes located at the corresponding pixel area and another biomolecule. In particular implementations, the pixel areas 1956A-1956D are illuminated by an excitation light (e.g., 532 nm). The pixel areas 1956A and 1956B are bound to respective biomolecules having light labels (e.g., fluorescent moieties). In response to the excitation stimulus, the pixel areas 1956A and 1956B provide light emissions as demonstrated in FIG. 19.

However, the pixel areas 1956 and the light sensors 1919 may be located relatively close to one another such that light emissions from a non-associated pixel area may be detected by a light sensor. Such light emissions may be referred to as crosstalk emissions or spatial crosstalk. By way of example, the light emissions propagating from the pixel area 1956A include a crosstalk signal and a pixel signal. The pixel signal of the light emissions from the pixel area 1956A is that signal of the light emissions that is configured to be detected by the light sensor 1919A. In other words, the pixel signal includes the light emissions that propagate at an angle that is generally toward the light sensor 1919A such that filter walls 1930 defining the detection path 1940A are capable of directing the light emissions toward the light sensor 1919A. The crosstalk signal is that signal of the light emissions that clears the filter walls 1930 defining the detection path 1940A and propagates into, for example, the detection path 1940B. In such cases, the crosstalk signal may be directed to the light sensor 1919B, which is not associated with the pixel area 1956A. Thus, the light sensor 1919B may be referred to as a non-associated light sensor with respect to the pixel area 1956A.

Using the implementation shown in FIG. 19 as an example, the light sensor 1919A may detect the pixel emissions from the pixel area 1956A and the crosstalk emissions from the pixel area 1956B. Likewise, the light sensor 1919B may detect the pixel emissions from the pixel area 1956B and the crosstalk emissions from the pixel area 1956A. The light sensor 1919C may detect the crosstalk emissions from the pixel area 1956B. However, the pixel area 1956C is not providing light emissions in FIG. 19. Thus, an amount of light detected by the light sensor 1919C is less than the corresponding amounts of light detected by the light sensors 1919A and 1919B. As shown in FIG. 19, the light sensor 1919C only detects crosstalk emissions from the pixel area 1956B, and the light sensor 1919D does not detect crosstalk emissions or pixel emissions.

Fading is an exponential decay in fluorescent signal intensity as a function of cycle number. As the sequencing run progress, the analyte strands are washed excessively, exposed to laser emissions that create reactive species, and subject to harsh environmental conditions. All of these lead to a gradual loss of fragments in each analyte, decreasing its fluorescent signal intensity. Fading is also called dimming or signal decay. FIG. 20 illustrates one example of fading 2000. In FIG. 20, the intensity values of analyte fragments with AC microsatellites show exponential decay.

Computer System

FIG. 21 is a computer system 2100 that can be used to implement the convolution-based base calling and the compact convolution-based base calling disclosed herein. Computer system 2100 includes at least one central processing unit (CPU) 2172 that communicates with a number of peripheral devices via bus subsystem 2155. These peripheral devices can include a storage subsystem 2110 including, for example, memory devices and a file storage subsystem 2121, user interface input devices 2138, user interface output devices 2176, and a network interface subsystem 2174. The input and output devices allow user interaction with computer system 2100. Network interface subsystem 2174 provides an interface to outside networks, including an interface to corresponding interface devices in other computer systems.

In one implementation, the model 623 is communicably linked to the storage subsystem 2110 and the user interface input devices 2138.

User interface input devices 2138 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2100.

User interface output devices 2176 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2100 to the user or to another machine or computer system.

Storage subsystem 2110 stores programming and data constructs that provide the functionality of some or all of the modules and methods described herein. These software modules are generally executed by deep learning processors 2178.

Deep learning processors 2178 can be graphics processing units (GPUs), field-programmable gate arrays (FPGAs), application-specific integrated circuits (ASICs), and/or coarse-grained reconfigurable architectures (CGRAs). Deep learning processors 2178 can be hosted by a deep learning cloud platform such as Google Cloud Platform™, Xilinx™, and Cirrascale™. Examples of deep learning processors 2178 include Google's Tensor Processing Unit (TPU)™, rackmount solutions like GX4 Rackmount Series™, GX21 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, and others.

Memory subsystem 2122 used in the storage subsystem 2110 can include a number of memories including a main random access memory (RAM) 2132 for storage of instructions and data during program execution and a read only memory (ROM) 2121 in which fixed instructions are stored. A file storage subsystem 2121 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2121 in the storage subsystem 2110, or in other machines accessible by the processor.

Bus subsystem 2155 provides a mechanism for letting the various components and subsystems of computer system 2100 communicate with each other as intended. Although bus subsystem 2155 is shown schematically as a single bus, alternative implementations of the bus subsystem can use multiple busses.

Computer system 2100 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2100 depicted in FIG. 21 is intended only as a specific example for purposes of illustrating the preferred implementations of the present invention. Many other configurations of computer system 2100 are possible having more or less components than the computer system depicted in FIG. 21.

Particular Implementations

We describe various implementations of determining tag signals from measured intensities. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

In one implementation, we disclose a computer-implemented method of determining tag signals from measured intensities. The measured intensities are collected by light sensors in a sensor array directed to a sample surface. The sample surface include pixel areas and hold a plurality of clusters during a sequence of sampling events. Each light sensor is directed to and measures intensity from one of the pixel areas during each sampling period.

An adjustment determiner 1702 determines an adjustment to the measured intensities from a pixel in the sampling periods for crosstalk from neighboring pixels by applying crosstalk estimations to measured intensities of the neighboring pixels in respective sampling periods.

The adjustment determiner 1702 determines a further adjustment to the measured intensities from the pixel in the sampling periods for background intensity.

The tag signals determiner 1704 determines the tag signals originating from the pixel in the sampling periods, takes into account the adjustment and the further adjustment to the measured intensities, combined with modifying at least the measured intensities to take into account signal decay over progress of the sequence and for phasing and pre-phasing.

The intensity modifier 1712 modifies the measured intensities in the sampling periods by a progressive decay function that takes into account how late each sampling period occurs in the sequence.

The distribution function applier 1714 applies a distribution function to at least current, prior and subsequent measured intensities, uses signal presence ground truth for the pixel in the sampling periods, and separates intensity contributions due to phasing and pre-phasing from contribution of a current tag signal to the current measured intensity.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

In one implementation, the distribution function for phasing and pre-phasing takes into account a broadening distribution over progress of the sequence. In one implementation, the broadening distribution is determined by repeatedly convolving a phasing kernel with itself.

In one implementation, the phasing kernel includes three terms for probabilities of sequence processing advancing as intended, failing to advance and skipping ahead by one position. In one implementation, the phasing kernel includes five terms for probabilities of sequence processing advancing as intended, failing to advance, skipping ahead by one position, skipping ahead by two positions, and skipping ahead by three positions.

In one implementation, the decay function is an exponential decay. In one implementation, the adjustment for background intensity is performed for the pixel using pixel-by-pixel background coefficients.

In one implementation, the adjustment for background intensity is a proportion between 0.95 and 0.995 of a minimum measured intensity for the pixel over the measured intensities in the sequence. In one implementation, the proportion is determined taking into account interaction between crosstalk from the neighboring pixels and the background adjustment for the pixel and the neighboring pixels.

In one implementation, the adjustment for crosstalk is performed for the pixel using a pixel-by-pixel crosstalk coefficients. In some implementations, a coefficients determiner 1722 determines coefficients for the crosstalk estimation and coefficients for the background intensity and coefficients for the decay function and coefficients for the distribution function by applying gradient descent to the signal presence ground truth for the pixel and the measured intensities for the sequence of the sampling events for the pixel.

In one implementation, the sampling events are applied to a known sample and the signal presence ground truth is based on reliable sequencing of the known sample translated to partial sequencing at the pixel. In one implementation, a trainer 1724 varies a learning rate for the gradient descent over training epochs.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

What is claimed is:

1. A computer-implemented method of determining tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling event, the computer-implemented method comprising:

adjusting a subset of the measured intensities from a pixel in the pixel areas for background intensity based on variations in background levels of the light sensors in the sensor array by removing a portion of a minimum measured intensity from the pixel; and determining an intensity of a tag signal originating from the pixel based on the adjusted subset of the measured intensities from the pixel.

2. The computer-implemented method of claim 1, wherein the adjustment for the background intensity is performed for the pixel using a pixel-by-pixel background coefficient.

3. The computer-implemented method of claim 2, wherein the pixel-by-pixel background coefficient is determined by background levels of the pixel and neighboring pixels.

4. The computer-implemented method of claim 1, wherein the adjustment for the background intensity is a proportion between 0.95 and 0.995 of the minimum measured intensity for the pixel over the measured intensities in the sequence of sampling events.

5. The computer-implemented method of claim 1, wherein the minimum measured intensity corresponds to a no signal condition.

6. A computer-implemented method of determining tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling event, the computer-implemented method comprising:
adjusting a subset of the measured intensities from a pixel in the pixel areas for crosstalk from neighboring pixels by using a pixel-by-pixel crosstalk coefficient that accounts for different background levels of the neighboring pixels; and
determining an intensity of a tag signal originating from the pixel based on the adjusted subset of the measured intensities from the pixel.

7. The computer-implemented method of claim 6, wherein the pixel-by-pixel crosstalk coefficient is determined by applying gradient descent to a signal presence ground truth for the pixel and the measured intensities for the sequence of the sampling events for the pixel.

8. The computer-implemented method of claim 7, wherein the sampling events of the sequence of sampling events are applied to a known sample, and the signal presence ground truth is based on reliable sequencing of the known sample translated to partial sequencing at the pixel.

9. The computer-implemented method of claim 8, further comprising varying a learning rate for the gradient descent over training epochs.

10. The computer-implemented method of claim 6, wherein the pixel-by-pixel crosstalk coefficient is determined based on the crosstalk from at least four neighboring pixels.

11. A computer-implemented method of determining tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling event, the computer-implemented method comprising:
determining, for a pixel in the pixel areas, coefficients for a progressive decay function;
adjusting a subset of the measured intensities from the pixel in the pixel areas using the coefficients for the progressive decay function to account for how late each sampling event occurs in the sequence of sampling events; and
determining an intensity of a tag signal originating from the pixel based on the adjusted subset of the measured intensities from the pixel.

12. The computer-implemented method of claim 11, wherein the progressive decay function accounts for an exponential signal decay in the subset of the measured intensities during the sequence of sampling events.

13. The computer-implemented method of claim 11, further comprising determining the coefficients for the progressive decay function by applying gradient descent to a signal presence ground truth for the pixel and the subset of the measured intensities for the pixel during the sequence of sampling events.

14. A computer-implemented method of determining tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling event, the computer-implemented method comprising:
correcting a subset of the measured intensities for phasing and pre-phasing events during the sequence of sampling events, by applying a distribution function to the subset of the measured intensities during a current sampling event, a prior sampling event, and a subsequent sampling event; and
determining an intensity of a tag signal originating from a pixel during the current sampling event from the corrected subset of the measured intensities.

15. The computer-implemented method of claim 14, wherein applying the distribution function to the subset of the measured intensities during the current sampling event, the prior sampling event, and the subsequent sampling event uses a signal presence ground truth for the pixel during the sequence of sampling events.

16. The computer-implemented method of claim 14, wherein determining the intensity of the tag signal includes separating intensity contributions due to the phasing and pre-phasing events from an intensity contribution of the tag signal during the current sampling event.

17. The computer-implemented method of claim 14, wherein the distribution function takes into account a broadening probability distribution over progress of the sequence of sampling events.

18. The computer-implemented method of claim 17, wherein the broadening probability distribution is determined by repeatedly convolving a phasing kernel with itself.

19. The computer-implemented method of claim 18, wherein the phasing kernel includes three terms for probabilities of sequence processing advancing as intended, failing to advance, and skipping ahead by one position.

20. The computer-implemented method of claim 18, wherein the phasing kernel includes five terms for probabilities of sequence processing advancing as intended, failing to advance, skipping ahead by one position, skipping ahead by two positions, and skipping ahead by three positions.

* * * * *